US008546533B2

(12) United States Patent
Martinez et al.

(10) Patent No.: US 8,546,533 B2
(45) Date of Patent: Oct. 1, 2013

(54) PIPECOLIC LINKER AND ITS USE FOR CHEMISTRY ON SOLID SUPPORT

(75) Inventors: Jean Martinez, Caux (FR); Pawel Zajdel, Cracovie (PL); Maciej Pawlowski, Wieliczka (PL); Gilles Subra, Saint Gely du Fesc (FR)

(73) Assignees: Centre National de la Recherche Scientifique (CNRS), Paris (FR); Universite de Montpellier 1, Montpellier (FR); Universite Jagellone, Kralow (PL); Universite Montpellier 2—Sciences et Techniques, Montpellier (FR)

( * ) Notice: Subject to any disclaimer, the term of this patent is extended or adjusted under 35 U.S.C. 154(b) by 288 days.

(21) Appl. No.: 13/061,080

(22) PCT Filed: Aug. 28, 2009

(86) PCT No.: PCT/EP2009/061171
§ 371 (c)(1),
(2), (4) Date: Feb. 25, 2011

(87) PCT Pub. No.: WO2010/023295
PCT Pub. Date: Mar. 4, 2010

(65) Prior Publication Data
US 2011/0152464 A1 Jun. 23, 2011

(30) Foreign Application Priority Data
Aug. 29, 2008 (EP) .................................... 08305512

(51) Int. Cl.
*C07K 1/02* (2006.01)
(52) U.S. Cl.
USPC ........................... 530/334; 530/333; 546/184
(58) Field of Classification Search
None
See application file for complete search history.

(56) References Cited

U.S. PATENT DOCUMENTS
7,244,815 B2   7/2007 Gutheil

FOREIGN PATENT DOCUMENTS
WO   WO 95/24186      9/1995
WO   WO 96/33972      10/1996
WO   WO 00/05243      2/2000
WO   WO 00/76974 A2   12/2000

OTHER PUBLICATIONS

Rabinowitz, Michael et al; "Solid phase/solution phase combinatorial synthesis of neuroimmunophilin ligands." Bioorg. and Med. Chem. Lett (2000)10 p. 1007-1010.*
Albericio et al., "Backbone Amide linker (BAL) for solid-phase synthesis of 2,5-piperazinediones (DKP), useful scaffolds for combinatorial chemistry", Frontiers of peptide science, proceedings of the American peptide symposium, 15th, Nashville (Jun. 14-19, 1997 1999b) pp. 37-39.
Albericio et al., "Solid-Phase Synthesis of 'Head-to-Tail' Cyclic and C-Terminal Modified Peptides", Innovation and Perspectives in solid phase synthesis & combinatorial libraries: Peptides, proteins, and nucleic acids-small molecule organic chemical diversity, collected papers, International symposium, 5th (Sep. 2-6, 1997 1999a) pp. 7-10.
Alsina et al., "Backbone Amide Linker (BAL) Strategy for Nα-9-Fluorenylmethoxycarbonyl (Fmoc) Solid-Phase Synthesis of Unprotected Peptide p-Nitroanilides and Thioesters", J. Organic Chemistry, vol. 64, No. 24 (1999) pp. 8761-8769.
Attardi et al., "Malachite green, a valuable reagent to monitor the presence of free COOH on the solid-phase", Tetrahedron Letters, vol. 41 (2000) pp. 7391-7394.
Balducci et al., "Stereocontrolled synthesis of unnatural cyclic dipeptides containing an L-valine unit", Tetrahedron: Asymmetry, vol. 16 (2005) pp. 1453-1462.
Barlos et al., "Anwendung von 4-Polystyryltriphenylmethylchiorid zur Synthese von Peptiden und Aminosäure-Derivaten", Liebigs Ann. Chem. (1988) pp. 1079-1081. (with English Abstract).
Bernhardt et al., "The solid-phase synthesis of side-chain-phosphorylated peptide-4-nitroanilides", J. Peptide Res., vol. 50 (1997) pp. 143-152.
Berst et al., "Solid-phase synthesis of apicidin A and a cyclic tetrapeptoid analogue", Chem. Commun. (2002) pp. 508-509.
Boschi et al., "NO-Donor Phenols: A New Class of Products Endowed With Antioxidant and Vasodilator Properties", J. Med. Chem. vol. 49 (2006) pp. 2886-2897.
Cantel et al., "Synthesis of Chiral α-Amino Aldehydes Linked by their Amine Function to Solid Support", J. Peptide Sci., vol. 10 (2004) pp. 531-534.
Cantel et al., "Synthesis of gem-diamio derivatives on solid support", Tetrahedron Letters, vol. 44 (2003) pp. 4797-4799.
European Search Report issued in EP Patent Application No. 08 30 5512 on Feb. 5, 2009.
Gutheil et al., "N-to-C Solid-Phase Peptide and Peptide Trifluoromethylketone Synthesis Using Amino Acid tert-Butyl Esters", Chem. Pharm. Bull., vol. 50, No. 5 (2002) pp. 686-691.
Hamze et al. "Solid-Phase Synthesis of Arginine-Containing Peptides and Fluorogenic Substrates Using a Side-Chain Anchoring Approach", J. Org. Chem., vol. 69 (2004) pp. 8394-8402.
International Search Report issued in PCT/EP2009/061171 on Nov. 3, 2009.
Jensen et al., "Backbone Amide Linker (BAL) Strategy for Solid-Phase Synthesis of C-Terminal-Modified and Cyclic Peptides1,2,3". J. Am. Chem. Soc., vol. 120 (1998) pp. 5541-5452.
Johansson et al., "An Improved Procedure for N- to C-Directed (Inverse) Solid-Phase Peptide Synthesis", J. Comb. Chem., vol. 2 (2000) pp. 496-507.
Lenstra et al., "(3S,6S)-3-Isopropyl-1,4-diazabicyclo[4.4.0]decane-2,5-dione, C11H18N2O2: Bayesian Statistics in Data Analysis", Acta Cryst., vol. B47 (1991) pp. 92-97.

(Continued)

*Primary Examiner* — Cecilia J Tsang
*Assistant Examiner* — Fred Reynolds
(74) *Attorney, Agent, or Firm* — Birch, Stewart, Kolasch & Birch, LLP.

(57) ABSTRACT

The present invention relates to a pipecolic linker and its use as a solid-phase linker in organic synthesis. Said pipecolic solid-phase linker may be used for coupling functional groups chosen between primary amines, secondary amines, aromatic amines, alcohols, phenols and thiols. In particular, said pipecolic solid-phase linker may be used for peptide or pseudopeptide synthesis, such as the reverse N to C peptide synthesis or the retro-inverso peptide synthesis, or for the synthesis of small organic molecules.

19 Claims, 3 Drawing Sheets

(56) References Cited

OTHER PUBLICATIONS

Figure 1:
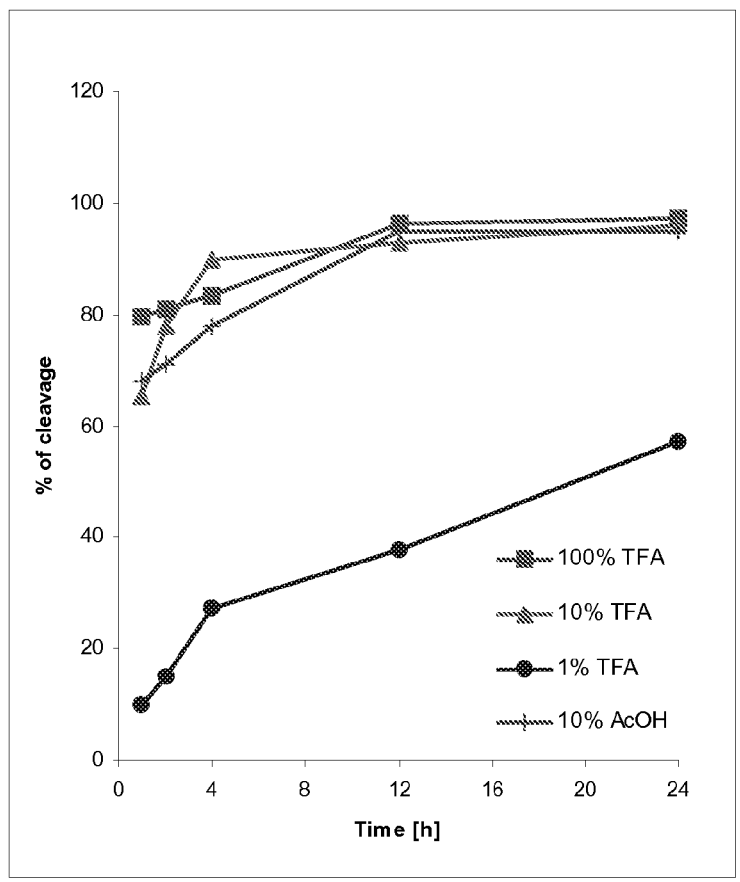

Maison et al., "Synthesis of novel pipecolic acid derivatives: a multicomponent approach from 3,4,5,6-tetrahydropyridines", J. Chem. Soc., Perkin Trans. 1 (1999) pp. 3515-3525.

Nam et al., "Reactions of Solid-Supported Reagents and Solid Supports with Alcohols and Phenols through Their Hydroxyl Functional Group", Journal of Combinatorial Chemistry, vol. 5, No. 5 (2003) pp. 479-546.

PCT Written Opinion of the International Searching Authority issued in PCT/EP2009/061171 on Nov. 3, 2009.

Rubini et al., "Mechanistic studies of amide bond scission during acidolytic deprotection of Pip containing peptide", J. Pept. Sci., vol. 14 (2008) pp. 989-997.

Strømgaard et al., "A Versatile Method for Solid-phase Synthesis of Polyamines: Neuroactive Polyamine Toxins as Example", Synthesis, No. 6 (2001) pp. 877-884.

Subra et al., "Glutamic acid as a new linker for attachment of alcohols to solid support", Tetrahedron Letters, vol. 43 (2002) pp. 9221-9223.

Wei et al., "Solid-Phase Synthesis of FKBP12 Inhibitors: N-Sulfonyl and N-Carbamoylprolyl/pipecolyl Amides", Bioorganic & Medicinal Chemistry Letters, vol. 12 (2002) pp. 1429-1433.

Zajdel et al., "A New Class of Arylpiperazine Derivatives: the Library Synthesis on SynPhase Lanterns and Biological Evaluation on Serotonin 5-HT1A and 5-HT2A Receptors", J. Comb. Chem., vol. 6 (2004) pp. 761-767.

Zajdel et al., "A New Highly Versatile Handle for Chemistry on a Solid Support: the Pipecolic Linker", Chem. Eur. J., vol. 16 (2010) pp. 7547-7553.

* cited by examiner

PIPECOLIC LINKER AND ITS USE FOR CHEMISTRY ON SOLID SUPPORT

The present invention relates to a pipecolic linker and its use as a solid-phase linker in organic synthesis. Said pipecolic solid-phase linker may be used for coupling functional groups chosen between primary amines, secondary amines, aromatic amines, alcohols, phenols and thiols. In particular, said pipecolic solid-phase linker may be used for peptide synthesis, such as reverse N to C peptide synthesis or C to N peptide synthesis, pseudopeptide synthesis, such as retro-inverso peptide synthesis, or synthesis of small organic molecules.

Since their introduction in 1963, solid supports became a routine tool for the peptide and pseudopeptide synthesis. Then, solid-phase synthesis of small organic molecules has emerged as an important tool for the generation of focused compound libraries. Accordingly, application of this strategy in pharmaceutical companies and academia has generally accelerated either hit identification or lead optimization within the drug discovery process.

Despite numerous advantages of solid supported chemistry for library generation, one of the crucial barriers during the synthetic steps is the stability of the functional group linking the first building block to the solid support. This anchor is performed through a linker designed to produce after deprotection a given functionality (i.e. carboxylic acids, primary amines, aldehydes . . . ) or a family of related functional groups. As a protecting group, the linker plays a key role in the choice of the synthetic strategy, determines conditions of the chemistry performed as well as conditions for anchoring and for releasing products from the solid support. These requirements seem to be the main obstacles to the wide-spread application of solid phase strategies for synthesis of diverse organic compounds. In this context, the development of both robust and versatile linker system is of high significance to speed up and facilitate the production of libraries.

Among targeted functionalities chosen for solid support anchoring, amines and alcohols are of high interest. That results from prevalent occurrence of these functionalities in the structures of biologically active compounds (Boschi et al., 2006; Nam et al., 2003; Stromgaard et al., 2001). Moreover, in the field of pseudopeptide and peptide chemistry these moieties represent special importance. Standard SPPS strategy relies on the anchoring of the C terminus of the carboxylic acid followed by C to N peptide elongation to minimize the epimerisation phenomenon. However, the interest in the search for new potent compounds as well as synthetic intermediates for either bioconjugation or ligation often necessitates modification at the C-terminus to introduce functionalities like alcohols, ethers, esters, thioesters, N-alkylamides, hydrazides, aldehydes or to obtain cyclic peptides. Such modifications may result in higher enzymatic stability and solubility of the obtained compounds, as well as in better ability to cross biological barriers. An alternative anchoring on solid support enables to maintain the peptide C-terminus free for further chemical modifications.

To achieve these goals, three main strategies can be distinguished: backbone anchoring through secondary amide bond, side chain anchoring of particular residues and N-terminus anchoring to the solid support.

The most important linker for backbone anchoring is the aldehyde functionalized linker e.g. BAL (backbone amide linker). This handle has been extensively used not only for the synthesis of C-terminal-modified (Albericio et al., 1999a; Alsina et al., 1999) and cyclic peptides (Jensen et al., 1998), but also for generation of small heterocyclic compounds (Albericio et al., 1999b).

The second strategy requires a specific linker adapted to anchor side-chain amino acid residue, e.g. guanidine group for Arginine (Hamze et al., 2004), alcohol for Serine and Threonine (Subra et al., 2002), amine for Ornithine and Lysine as well as carboxylic acid for Aspartic and Glutamic acids. It is worth to note, that this approach enables simultaneous modification of peptide at the N- and C-terminus.

Finally, the N-terminus anchoring strategy is principally set up when one needs to perform SPPS in the reverse direction. This strategy is of growing interest for peptide mimetic synthesis, leaving carboxylic acid functions ready to undergo chemical transformations. For this purpose, a convenient linker is required to attach the N-terminal amine to the solid support. (Cantel et al., 2004; Cantel et al., 2003).

These considerations prompted the Inventors to develop a versatile linker suitable for immobilization of electron-rich moieties including amines and alcohols that could be applied to solid phase organic chemistry as well as to peptide and pseudopeptide chemistry by side-chain or N-terminus anchoring.

Among linkers, TFA-labile handles are especially useful for the production of combinatorial libraries. Indeed, by using that methodology cleavage and post-cleavage workups are straightforward and often require only simple evaporation of TFA that can be done in parallel using vacuum centrifugator or inert gas bubbling.

Commercially available acid-labile linkers are not so common for efficient anchoring and releasing of amine or alcohol groups containing compounds. Hindered trityl related linkers, such as 2-chloro chlorotrityl or 4-carboxy chlorotrityl linkers, provide a direct route to the anchoring of a wide variety of nucleophiles. However, loading efficiency significantly decrease when bulky or unreactive nucleophiles such as aromatic amines or alcohols are used. Moreover, trityl based linkers are very sensitive to acidic treatment that can be a great advantage but can be a drawback when mild acidic conditions are required during the solid supported synthetic route for the target compounds. The main alternative to direct immobilization of amines or alcohol is the use of carbamate or carbonate linkage built on alcohol functionalized resin such as acid labile hydroxymethylphenoxy linker (Wang resin as an example), HMBA linker or simply HF-labile hydroxymethyl polystyrene support. However, prior to the immobilization of the first building block, this strategy requires derivatization of the alcohol linker as an activated intermediate like p-nitrophenylcarbonate or imidazole carbonate and the loading yields are usually very low. In addition to this drawback, this kind of linkage is not always stable towards nucleophilic attack (Cantel et al., 2004).

The present invention relates to the design and the use of a novel acid-labile linker based on the pipecolic acid scaffold. The carboxylic function of this linker can be readily activated to anchor nucleophiles such as amines or alcohols through amide or ester bond respectively (see part III of the Examples, Synthesis scheme no 2). The linker can accommodate a wide range of building-blocks and its use is demonstrated for side chain and N-terminus anchoring of peptides and pseudopeptides. The peptides or pseudopeptides can then be released from the pipecolic linker solid support by acidic hydrolysis. It is believed that said acidic hydrolysis is favored by the spatial properties of the pipecolic linker and is reinforced by the nature of the $R_1$ substituents.

In a first aspect, the present invention relates to a solid phase-linker combination having the following formula:

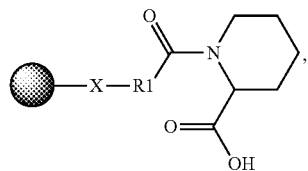

(I)

wherein

represents a solid support used in organic synthesis,

X is absent or represents —NR—, —NR$_2$—CO—, —S—CO—, —O—, —CO—NR$_2$—, —S—, —CO—S—, —CO—O—, —O—CO—, —SO$_2$—NR$_2$— or —NR$_2$SO$_2$— wherein R$_2$ represents H or a (C$_1$-C$_6$) alkyl, advantageously H, it being understood that X can be separated from the solid support by means of a spacer, and R$_1$ represents a branched (C$_3$-C$_{30}$) alkyl group, a branched (C$_3$-C$_{30}$) alkenyl group, a branched (C$_3$-C$_{30}$) alkynyl group, a (C$_4$-C$_{12}$) monocyclic or polycyclic hydrocarbonated group, a (C$_1$-C$_6$) alkyl-(C$_4$-C$_{12}$) monocyclic or polycyclic hydrocarbonated group, a (C$_2$-C$_6$) alkenyl-(C$_4$-C$_{12}$) monocyclic or polycyclic hydrocarbonated group, or a (C$_2$-C$_6$) alkynyl-(C$_4$-C$_{12}$) monocyclic or polycyclic hydrocarbonated group.

In the present invention, the solid phase-linker combination of formula (I) can also be named "pipecolic linker solid support".

The terms "solid support", "solid phase", "matrix" and "resin" refer indifferently in the present invention to a support conventionally used in organic chemistry, and particularly in peptide synthesis. Advantageously, the solid support is chosen among the polystyrene supports, polyamide supports, polyethylene glycol supports, polyacrylic supports, composite supports and copolymers thereof, such as polyacrylic/beta-alanine copolymer supports, polyacrylamide/polystyrene copolymer supports, polyacrylamide/polyethylene glycol copolymer supports and polethyleneglycol/polystyrene copolymer supports, it being possible for said support to be in the form of beads, of a film-coated support such as rings or lanterns, of a plug, or of a noncrosslinked soluble support.

More advantageously, the solid support is selected from:
(i) beads of gelatinous or macroporous resins having a matrix with a polystyrene (PS) base, or having a matrix with a polyamide (PL) or polyethylene glycol base (PEG), or else composite supports of polyethylene glycol-polystyrene (PEG-PS) or polyethylene glycol-dimethylacrylamide (PEGA) type, and
(ii) film-coated supports such as SynPhase Lanterns® (Mimotopes, Australia), that are constituted of a mobile surface polymer grafted onto a rigid unreactive base polymer, the unique "Lantern" shape providing maximized surface area, free flow-through of reactants and rapid drainage of wash solutions.

In the present invention, when X is absent, the group R$_1$ is directly linked to the solid support.

Alternatively, when X is present, X is derived from the anchoring of the pipecolic linker of formula (XI) as disclosed below to the functionalized solid support. The solid support of the present invention is functionalized with a function preX capable to react with the pipecolic linker in which R$_1$ has been functionalized with a functional group Y by a process well known from the one skilled in the art. For example, a support carrying the function —NH$_2$ will react with the pipecolic linker of formula (XI) in which R$_1$ has been functionalized with Y=—COOH, thus obtaining X being —NH—CO— (see part I of the Examples, Synthesis scheme no 1 where R$_1$ is a cyclohexyl group). In another example, a support carrying the function —COOH will react with the pipecolic linker of formula (XI) in which R$_1$ has been functionalized with Y=—NH$_2$, thus obtaining X being —CO—NH—. The function of the solid support which reacts with Y of the functionalized pipecolic linker will be named herein "preX" for more comprehension (in Synthesis scheme no 1, preX=NH$_2$). Therefore, by the reaction between preX and Y, X is obtained.

Preferably, X represents —O—CO—, —NH—CO—, —CO—O— or —CO—NH—, more preferably —O—CO— or —NH—CO—, still more preferably —NH—CO—.

Advantageously, the solid support functionalized with the function preX is a chloromethyl polystyrene resin in which the function preX is Cl—CH$_2$—, a benzyloxybenzyl alcohol polystyrene resin in which the function preX HO—, an aminomethyl polystyrene (AM-PS) resin in which the function preX is NH$_2$—, or a methylbenzhydrylamine polystyrene resin such as a 4-methylbenzhydrylamine polystyrene resin, in which the function preX is NH$_2$—. More advantageously, the solid support functionalized with the function preX is an aminomethyl polystyrene (AM-PS) resin or a 4-methylbenzhydrylamine polystyrene resin.

In the present invention, X can also be separated from the solid support by means of a spacer. The terms "arm" and "spacer" are used indifferently in the present invention and refer to any fragment well known and commonly used by the skilled person, in particular one used for peptide synthesis, which can be grafted to the solid support. In the case of X being separated from the solid support by means of a spacer, it should be understood that X is derived from the function preX which is contained in the spacer. Advantageously, the fragment is chosen among Rink amide (Rink signifying 4-[2', 4'-dimethoxyphenyl-(9-fluoromethyloxycarbonyl)aminomethyl]phenoxy-) containing the function preX=NH$_2$—, chlorotrityl containing the function preX=Cl—C, hydroxymethylbenzylacetamide containing the function preX=HO—, Sieber amide (Sieber signifying 9-aminoxanthen-3-yloxy-) containing the function preX=NH$_2$—, aminomethyl-3,5-dimethoxyphenoxyalkyl containing the function preX=NH$_2$—, aminomethyl-3-dimethoxyphenoxyalkyl containing the function preX=NH$_2$—, hydroxymethyl-3,5-dimethoxyphenoxyalkyl containing the function preX=OH—, and hydroxymethyl-3-dimethoxyphenoxyalkyl containing the function preX=OH—.

Within the framework of the present invention, "(C$_1$-C$_6$) alkyl" means any linear or branched saturated hydrocarbon radical having from one to six carbon atoms. Examples of (C$_1$-C$_6$) alkyl radicals include, but are not limited to, methyl, ethyl, n-propyl, isopropyl, 1-ethylpropyl, sec-butyl, iso-butyl, tert-butyl, n-butyl, n-pentyl, n-hexyl, etc.

Within the framework of the present invention, "branched (C$_3$-C$_{30}$) alkyl group" means any branched saturated hydrocarbon radical having from three to thirty carbon atoms. Examples of branched (C$_3$-C$_{30}$) alkyl radicals include, but are not limited to, isopropyl, 1-ethylpropyl, sec-butyl, ter-butyl, isohexadecyl, etc.

Within the framework of the present invention, "branched (C$_3$-C$_{30}$) alkenyl group" means any branched hydrocarbon alkenyl radical having from three to thirty carbon atoms.

Examples of branched ($C_3$-$C_{30}$) alkenyl radicals include, but are not limited to isopropenyl, isobutenyl, sec-butenyl, tert-butenyl, isopentenyl, etc.

Within the framework of the present invention, "branched ($C_3$-$C_{30}$) alkynyl group" means any branched hydrocarbon alkynyl radical having from three to thirty carbon atoms. Examples of branched ($C_3$-$C_{30}$) alkynyl radicals include, but are not limited to isobutynyl, isopentynyl, etc.

In the present invention, the expressions "monocyclic or polycyclic hydrocarbonated group", "monocyclic or polycycloalkyl group" and "monocyclic or polycyclic cycloalkyl group" are used indifferently.

"($C_4$-$C_{12}$) monocyclic or polycyclic hydrocarbonated group", also named "($C_4$-$C_{12}$) monocyclic or polycycloalkyl group", refers indifferently in the present invention to a saturated hydrocarbonated group consisting of one or more cycles, advantageously 1, 2, 3, 4, 5 or 6 cycles, advantageously 1, 2 or 3 cycles, each cycle being a 4-, 5-, 6- or 7-membered cycle, more advantageously a 5-, or 6-membered cycle. It should be also understood that in the case where the polycyclic group consists in 2 cycles, said cycles may be fused or bridged together, or can be linked together by a spiro junction, or that a carbon atom of one cycle of the ($C_4$-$C_{12}$) polycyclic hydrocarbonated group forms a covalent bound with a carbon atom of another cycle of the ($C_4$-$C_{12}$) polycyclic hydrocarbonated group.

For example, a bicyclic hydrocarbonated group in which each cycle is a 6-membered cycle can be:

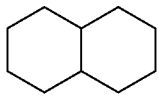

fused,

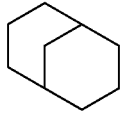

bridged,

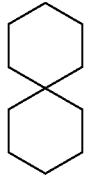 [SMILES: C1CCC2(CC1)CCCCC2]

with a junction spiro,

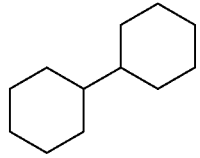 [SMILES: C1CCC(C2CCCCC2)CC1]

with a C—C bound.

In the case where the polycyclic group consists in more than 2 cycles, the skilled person will understand that there may be a combination of these cycle configurations.

It should be also understood that one or more of said cycles of the ($C_4$-$C_{12}$) monocyclic or polycyclic hydrocarbonated group may be an heterocycle, which means that said cycles incorporate one or more, advantageously one or two heteroatoms (selected advantageously from nitrogen, oxygen or sulfur atom).

Other examples of ($C_4$-$C_{12}$) monocyclic or polycyclic hydrocarbonated group include cyclopentyl, cyclohexyl, cycloheptyl, adamantyl or norbornyl group. Advantageously, ($C_4$-$C_{12}$) monocyclic or polycyclic hydrocarbonated group is a ($C_5$-$C_{10}$) monocyclic or polycyclic hydrocarbonated group, more advantageously a $C_5$ or $C_6$ monocyclic or polycyclic hydrocarbonated group. More advantageously, the ($C_4$-$C_{12}$) monocyclic or polycyclic hydrocarbonated group is a cyclopentyl, cyclohexyl, adamantyl or norbornyl group.

"($C_1$-$C_6$) alkyl-($C_4$-$C_{12}$) monocyclic or polycyclic hydrocarbonated group" means any ($C_4$-$C_{12}$) monocyclic or polycyclic hydrocarbonated group such as defined above, linked to the X or Y group or to the solid support by means of a ($C_1$-$C_6$) alkyl group such as defined above. Furthermore, in the case of a ($C_1$-$C_6$) alkyl-($C_4$-$C_{12}$) monocyclic or polycyclic hydrocarbonated group, the ($C_4$-$C_{12}$) monocyclic or polycyclic hydrocarbonated group may in addition refer to unsaturated or partially saturated hydrocarbonated groups, such as for example monocyclic or polycyclic hydrocarbonated groups in which respectively the cycle or at least one cycle of the polycyclic hydrocarbonated group, advantageously all the cycles of the polycyclic hydrocarbonated group, is an aryl cycle, advantageously a phenyl cycle.

"($C_2$-$C_6$) alkenyl-($C_4$-$C_{12}$) monocyclic or polycyclic hydrocarbonated group" means any ($C_4$-$C_{12}$) monocyclic or polycyclic hydrocarbonated group such as defined above, linked to the X or Y group or to the solid support by means of a ($C_2$-$C_6$) alkenyl group. "($C_2$-$C_6$) alkenyl group" means any linear or branched hydrocarbon alkenyl radical having from two to six carbon atoms. Examples of ($C_2$-$C_6$) alkenyl radicals include, but are not limited to, ethenyl, propenyl, butenyl, pentenyl, etc. In the case of a ($C_2$-$C_6$) alkenyl-($C_4$-$C_{12}$) monocyclic or polycyclic hydrocarbonated group, the ($C_4$-$C_{12}$) monocyclic or polycyclic hydrocarbonated group may in addition refer to unsaturated or partially saturated hydrocarbonated groups, such as for example monocyclic or polycyclic hydrocarbonated groups in which respectively the cycle or at least one cycle of the polycyclic hydrocarbonated group, advantageously all the cycles of the polycyclic hydrocarbonated group, is an aryl cycle, advantageously a phenyl cycle.

"($C_2$-$C_6$) alkynyl-($C_4$-$C_{12}$) monocyclic or polycyclic hydrocarbonated group" means any ($C_4$-$C_{12}$) monocyclic or polycyclic hydrocarbonated group such as defined above, linked to the X or Y group or to the solid support by means of a ($C_2$-$C_6$) alkynyl group. "($C_2$-$C_6$) alkynyl group" means any linear or branched hydrocarbon alkynyl radical having from two to six carbon atoms. Examples of ($C_2$-$C_6$) alkynyl radicals include, but are not limited to, ethynyl, propynyl, 1-butynyl, etc. In the case of a ($C_2$-$C_6$) alkynyl-($C_4$-$C_{12}$) monocyclic or polycyclic hydrocarbonated group, the ($C_4$-$C_{12}$) monocyclic or polycyclic hydrocarbonated group may in addition refer to unsaturated or partially saturated hydrocarbonated groups, such as for example monocyclic or polycyclic hydrocarbonated groups in which respectively the cycle or at least one cycle of the polycyclic hydrocarbonated group, advantageously all the cycles of the polycyclic hydrocarbonated group, is an aryl cycle, advantageously a phenyl cycle.

Advantageously, one or more of the cycles of the $(C_1-C_6)$ alkyl-$(C_4-C_{12})$ unsaturated or partially saturated monocyclic or polycyclic hydrocarbonated group, $(C_2-C_6)$ alkenyl-$(C_4-C_{12})$ unsaturated or partially saturated monocyclic or polycyclic hydrocarbonated group, or $(C_2-C_6)$ alkynyl-$(C_4-C_{12})$ unsaturated or partially saturated monocyclic or polycyclic hydrocarbonated group, may be an heterocycle incorporating one or more, advantageously one or two heteroatoms (advantageously a nitrogen, oxygen or sulfur atom).

More advantageously, the "$(C_1-C_6)$ alkyl-$(C_4-C_{12})$ monocyclic or polycyclic hydrocarbonated group" is a "$(C_1-C_3)$ alkyl-$(C_5-C_{10})$ monocyclic or polycyclic hydrocarbonated group. Even more advantageously, the $(C_1-C_6)$ alkyl-$(C_4-C_{12})$ monocyclic or polycyclic hydrocarbonated group is a methyl-$C_5$ or $C_6$ monocyclic or polycyclic hydrocarbonated group. Most advantageously, the $(C_1-C_6)$ alkyl-$(C_4-C_{12})$ monocyclic or polycyclic hydrocarbonated group is norborn-2-yl-methyl group.

In a particularly preferred embodiment of the present invention, the solid phase-linker combination is represented by the formula selected from the following formulae:

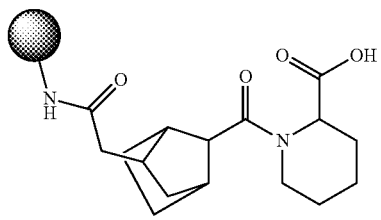

(Ia)

wherein is as defined above, $R_1$ is a norborn-2-yl-methyl and X is —NH—CO—,

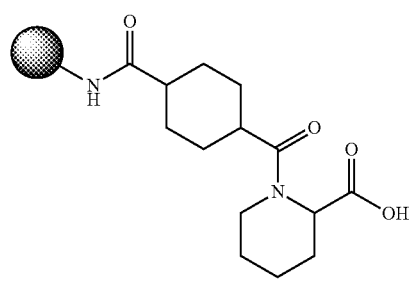

(Ib)

wherein is as defined above, $R_1$ is a cyclohexyl and X is —NH—CO—, and

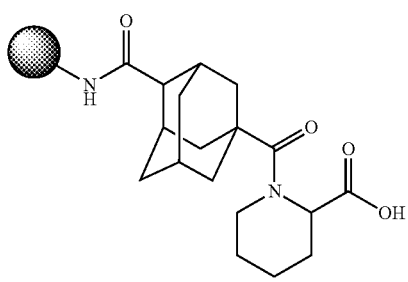

(Ic)

wherein

is as defined above, $R_1$ is an adamantyl and X is —NH—CO—.

The invention also relates to a process for preparing the solid phase-linker combination of formula (I) according to the present invention, wherein it comprises the step (d1) of deprotection of the solid phase linker combination of the following formula

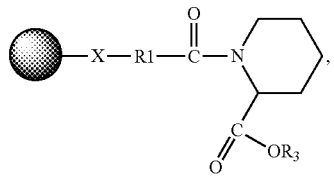

(II)

wherein $R_1$ is as defined above.
$R_3$ is a O-protecting group,

and X are as defined above.

Within the framework of the present invention, the term "O-protecting group" refers herein to a substituent which protects hydroxyl groups against undesirable reactions during synthetic procedures such as the O-protecting groups disclosed in Greene, "Protective Groups In Organic synthesis", (John Wiley & Sons, New York (1981)). O-protecting groups comprise substituted methyl ethers, for example, methoxymethyl (MOM), benzyloxymethyl, 2-methoxyethoxymethyl, 2-(trimethylsilyl)ethoxymethyl, t-butyl, benzyl and triphenylmethyl, tetrahydropyranyl ethers, substituted ethyl ethers, for example, 2,2,2-trichloroethyl, silyl ethers, for example, trimethylsilyl, t-butyldimethylsilyl (TBS) and t-butyldiphenylsilyl; and esters prepared by reacting the hydroxyl group with a carboxylic acid for example, acetate, propionate, benzoate and the like.

In a preferred embodiment, the O-protecting group $R_3$ is a $(C_1-C_6)$ alkyl, advantageously a methyl, and the deprotection step (d1) is carried out by saponification with a solution of LiOH in a solvent such as tetrahydrofurane.

Advantageously, the solid phase linker combination of formula (II) is obtained by (c1) reaction of the solid phase linker combination of formula

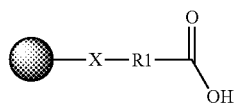

wherein

X and $R_1$ are as defined above,
with a compound of formula

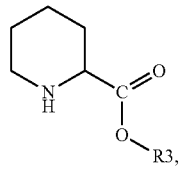

wherein $R_3$ is as defined above. Advantageously, $R_3$ is a $(C_1-C_6)$ alkyl, more advantageously a methyl.

In a further preferred embodiment, the reaction step (c1) is carried out under O-(1H-benzotriazol-1-yl)-1,1,3,3-tetramethylphosphonium hexafluorophosphate-promoted amide coupling in the presence of triethylamine in a solvent such as dimethylformamide.

In an advantageous embodiment, the solid phase linker combination of formula (III) is obtained by:
(a1) reaction of a functionalized solid phase of formula

wherein

is as defined above and preX is a functional group of the solid support which reacts, in order to obtain X, with the functional group Y of the compound of formula

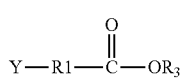

wherein $R_1$ and $R_3$ are as defined above, and
(b1) capping with an appropriate capping group the functions -preX of the solid phase linker combination of formula (V) which did not react with Y of the compound of formula (VI).

The term "capping group" refers herein to a substituent which protects the functions -preX of the solid support which did not react with the compound of formula (VI). This allows blocking said functions against undesirable reactions during use of the solid-phase linker combination of formula (I) in subsequent applications such as peptide synthesis. The capping groups are well known by the skilled person and will be selected in accordance with the function -preX of the solid support.

More preferably, when the function -preX is —$NH_2$, the appropriate capping group used in the capping step (b1) is the N-protecting group acetyl, and the capping step (b1) is carried out by using acetic anhydride in a solvent such as dichloromethane.

An advantageous step (a1) is that where -preX is —$NH_2$ and Y is —COOH.

Advantageously, the step (a1) is carried out using a coupling mixture comprising diisopropylcarbodiimide and hydroxybenzotriazole in a solvent, such as dimethylformamide. Such a coupling mixture is very appropriate when -preX is —$NH_2$ but it can also be used with other functions, such as when preX is —OH. Another coupling mixture which can be used is 4-dimethylaminopyridine in presence of diisopropylcarbodiimide, in particular when -preX is —OH.

The process for preparing the solid phase linker combination of formula (I) is embodied in part I of the Examples and in Synthesis scheme no 1 below.

The invention also relates to a process for preparing the solid phase-linker combination of formula (I) according to the present invention, wherein the compound of formula (XI) as defined below is functionalized with the functional group Y and is coupled with the compound of formula (V) as defined above.

The present invention also relates to a compound having the following formula:

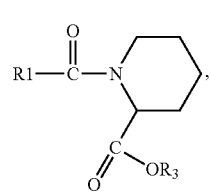

wherein $R_1$ and $R_3$ are as defined above.

In the present invention, the compound of formula (XI) will be called the "pipecolic linker".

Advantageously, $R_3$ is a $(C_1-C_6)$ alkyl, more advantageously a methyl.

Advantageously, $R_1$ is functionalized with a functional group Y by a process well known by the one skilled in the art, in which Y is as defined above.

Advantageously, Y represents —OH, —COOH, —$NHR_2$, —$SO_2$, —$SO_3H$ or —SH. More advantageously, Y is —COOH or —$NH_2$, still more advantageously —COOH.

Preferably, $R_1$ is a $(C_5-C_{10})$ monocyclic or polycyclic hydrocarbonated group, more preferably a $C_5$ or $C_6$ monocyclic or polycyclic hydrocarbonated group. In an alternative preferred embodiment, $R_1$ is a $(C_1-C_3)$ alkyl-$(C_5-C_{10})$ monocyclic or polycyclic hydrocarbonated group, more preferably a methyl-$C_5$ or $C_6$ monocyclic or polycyclic hydrocarbonated group.

In a particularly preferred embodiment of the present invention, the pipecolic linker is represented by the formula selected from the following formulae:

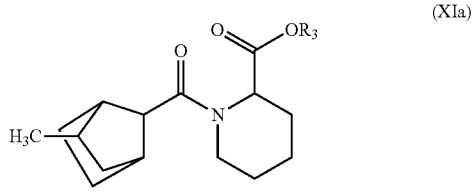

in which $R_1$ is a norborn-2-yl-methyl and $R_1$ is advantageously functionalized with a functional group Y, and $R_3$ is as defined above,

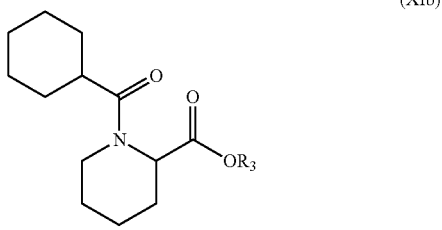

in which $R_1$ is a cyclohexyl and $R_1$ is advantageously functionalized with a functional group Y, and $R_3$ is as defined above, and

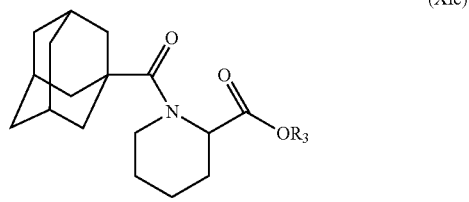

in which $R_1$ is an adamantyl and $R_1$ is advantageously functionalized with a functional group Y, and $R_3$ is as defined above.

Advantageously, $R_3$ is a ($C_1$-$C_6$) alkyl, more advantageously a methyl.

The present invention also relates to the use of the compound having the formula (XI) as defined above, as a solid-phase linker.

In a further aspect, the invention relates to the use of the solid phase linker combination of formula (I) according to the present invention for coupling functional groups chosen between primary amines, secondary amines, aromatic amines, alcohols, phenols and thiols.

The Synthesis scheme no 2 below (part III of the Examples) discloses the general use of the solid phase linker combination of formula (I) according the present invention.

The coupling reaction may be carried out using appropriate coupling reagents which are well known by the skilled person, such as DIC/HOBt, DIC/HOAt, DCC/HOSu, DCC/HOBT, PyBop/DIEA, PyBrop/NMM, HBTU/TEA, EDC/HOBt and the like. Advantageously, the use of the solid phase linker combination of formula (I) according to the invention is for coupling secondary and primary non aromatic amines, wherein the coupling reaction is carried out using O-(1H-benzotriazol-1-yl)-1,1,3,3-tetramethylphosphonium hexafluorophosphate activation in the presence of diisopropylethylamine in a solvent such as dimethylformamide.

In another advantageous embodiment, the use of the solid phase linker combination of formula (I) according to the invention is for coupling primary aromatic amines, wherein the coupling reaction is carried out using N-[(dimethylamino)-1H-1,2,3-triazolo-[4,5-b]pyridine-1-yl-methylene]-N-methylmethanaminium hexafluorophosphate N-oxide activation in the presence of 2,4,6 trimethylpyridine in a solvent such as dimethylformamide.

The invention also relates to the use of the solid phase-linker combination of formula (I) according to the present invention for the synthesis of small organic molecules such as for example piperazin-1-yl-M-tolyl-methanone.

The invention further relates to the use of the solid phase-linker combination of formula (I) according to the present invention for reverse N to C peptide synthesis, C to N peptide synthesis or pseudopeptide synthesis, such as retro-inverso peptide synthesis.

More particularly, the invention relates to a reverse N to C peptide synthesis process comprising the following successive steps:

(a2) coupling the solid phase linker combination of formula (I) according to the present invention with COO-protected amino acids in which the reactive functions of the amino acid lateral chains are protected in order to obtain COO-protected amino acids coupled with the solid phase linker combination, (b2) COO-deprotecting the amino acids coupled with the solid phase linker combination, (c2) coupling the COO-deprotected amino acids coupled with the solid phase linker combination obtained in step (b2) with COO-protected amino acids in which the reactive functions of the amino acids lateral chains are protected in order to obtain COO-protected peptides coupled with the solid phase linker combination, (d2) optionally repeating steps (b2) and (c2) as many times as necessary in order to obtain a solid phase linker combination loaded with peptidic chains, (e2) cleaving the bond between the solid phase linker combination and the peptidic chains in order to recover the solid phase linker combination of formula (I) and peptidic chains.

The term "COO-protected amino acid" refers herein to an amino-acid whose COO— group is protected by a substituent in order to avoid undesirable reactions during synthetic procedures. The COO-protecting groups of the COO-protected amino acids are disclosed in Greene, "Protective Groups in Organic synthesis", (John Wiley & Sons, New York (1981). COO-protecting groups comprise substituted methyl ethers, for example, methoxymethyl (MOM), benzyloxymethyl, 2-methoxyethoxymethyl, 2-(trimethylsilyl)ethoxymethyl, t-butyl, benzyl and triphenylmethyl, tetrahydropyranyl ethers, substituted ethyl ethers, for example, 2,2,2-trichloroethyl, silyl ethers, for example, trimethylsilyl, t-butyldimethylsilyl (TBS) and t-butyldiphenylsilyl; and esters prepared by reacting the hydroxyl group with a carboxylic acid for example, acetate, propionate, benzoate and the like. In particular the COO-protecting group of the COO-protected amino acid is a ($C_1$-$C_6$) alkyl group, advantageously a methyl, and the COO-deprotecting step (b2) is carried out by saponification with a solution of LiOH in a solvent such as tetrahydrofurane.

Moreover, in the present invention, the reactive functions of the amino acid lateral chains may be protected against undesirable reactions during synthetic procedures using appropriate substituents well known by the skilled person.

In the sense of the present invention, "amino acids" means all natural α-amino acid residues (for example alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophane (Trp), tyrosine (Tyr) and valine (Val)) in D or L form, as well as non-natural amino acids (for example, β-alanine, allylglycine, tert-leucine, norleucine (Nle), 3-amino-adipic acid, 2-aminobenzoic acid, 3-aminobenzoic acid, 4-aminobenzoic acid, 2-aminobutanoic acid, 4-amino-1-carboxymethyl piperidine, 1-amino-1-cyclobutanecarboxylic acid, 4-amino cyclohexaneacetic acid, 1-amino-1-cyclohexanecarboxylic acid, (1R,2R)-2-amino cyclohexanecarboxylic acid, (1R,2S)-2-amino cyclohexanecarboxylic acid, (1S,2R)-2-amino cyclohexanecarboxylic acid, (1S,2S)-2-aminocyclohexanecarboxylic acid, 3-aminocyclohexanecarboxylic acid, 4-amino cyclohexanecarboxylic acid, (1R,2R)-2-amino cyclopentanecarboxylic acid, (1R,2S)-2-amino cyclopentanecarboxylic acid 1-amino-1-cyclopentanecarboxylic acid, 1-amino-1-cyclopropanecarboxylic acid, 4-(2-aminoethoxy)-benzoic acid, 3-aminomethylbenzoic acid, 4-aminomethylbenzoic acid, 2-aminobutanoic acid, 4-aminobutanoic acid, 6-aminohexanoic acid, 1-aminoindane-1-carboxylic acid, 4-aminomethyl-phenylacetic acid, 4-aminophenylacetic acid, 3-amino-2-naphthoic acid, 4-aminophenylbutanoic acid, 4-amino-5-(3-indolyl)-pentanoic acid, (4R,5S)-4-amino-5-methylheptanoic acid, (R)-4-amino-5-methylhexanoic acid, (R)-4-amino-6-methylthiohexanoic acid, (S)-4-amino-pentanoic acid, (R)-4-amino-5-phenylpentanoic acid, 4-aminophenylpropionic acid, (R)-4-aminopimeric acid, (4R,5R)-4-amino-5-hyroxyhexanoic acid, (R)-4-amino-5-hydroxypentanoic acid, (R)-4-amino-5-(p-hydroxyphenyl)-pentanoic acid, 8-aminooctanoic acid, (2S,4R)-4-amino-pyrrolidine-2-carboxylic acid, (2S,4S)-4-amino-pyrrolidine-2-carboxylic acid, azetidine-2-carboxylic acid, (2S,4R)-4-benzyl-pyrrolidine-2-carboxylic acid, (S)-4,8-diaminooctanoic acid, tert-butylglycine, γ-carboxyglutamate, β-cyclohexylalanine, citruline, 2,3-diamino propionic acid, hippuric acid, homocyclohexylalanine, moleucine, homophenylalanine, 4-hydroxyproline, indoline-2-carboxylic acid, isonipecotic acid, α-methyl-alanine, nicopetic acid, norvaline, octahydroindole-2-carboxylic acid, ornithine, penicillamine, phenylglycine (Phg), 4-phenyl-pyrrolidine-2-carboxylic acid, propargylglycine, 3-pyridinylalanine, 4-pyridinylalanine, 1-pyrrolidine-3-carboxylic acid, sarcosine, the statins, tetrahydroisoquinoline-1-carboxylic acid, 1,2,3,4-tetrahydroisoquinoline-3-carboxylic acid, tranexamic acid, 4,4-difluoro proline, 4-fluoro proline, alpha-(3,4-difluorobenzyl)-proline, gamma-(3,4-difluorobenzyl)-proline, alpha-(trifluoromethyl)phenylalanine, hexafluoroleucine, 5,5,5-trifluoroleucine, 6,6,6-trifluoronorleucine, 2-(trifluoromethyl)leucine, 2-(trifluoromethyl)norleucine, 4,4,4-trifluorovaline, 4,4,4,4',4',4'-hexafluorovaline, pentafluorophenylalanine, 2,3-difluorophenylalanine, 2,4-difluorophenylalanine, 2,5-difluorophenylalanine, 2,6-difluorophenylalanine, 3,4-difluorophenylalanine, 3,5-difluorophenylalanine, 3,3-difluoro-3-(4-fluorophenyl)alanine, 2,3-difluorophenylglycine, 2,4-difluorophenylglycine, 2,5-difluorophenylglycine, 3,4-difluorophenylglycine, 4,4-difluoroethylglycine, 4,4,4-trifluoroethylglycine and hexafluoronorleucine).

In the sense of the present invention, the term "peptide" refers to a sequence of amino acids as defined above. The sequence can be linear or cyclic. For example, a cyclic peptide can result from the formation of a disulfide bridge between two cysteine residues in a sequence. In another example, a cyclic peptide can result from the formation of an amine bond between its Nter- and its Cter-parts, or between the lateral chains of the amino-acids Asp and Lys. Techniques for cyclizing a peptide and for obtaining a cyclic peptide using a solid support are well known by the man skilled in the art.

The coupling step (a2) and/or (c2) may be carried out under O-(1H-benzotriazol-1-yl)-1,1,3,3-tetramethylphosphonium hexafluorophosphate activation in the presence of diisopropylethylamine in a solvent such as dimethylformamide.

In another preferred embodiment, the coupling step (a2) and/or (c2) is carried out under N-[(dimethylamino)-1H-1,2,3-triazolo-[4,5-b]pyridin-1-yl-methylene]-N-methylmethanaminium hexafluorophosphate N-oxide activation in the presence of 2,4,6 trimethylpyridine in a solvent such as dimethylformamide, in order to avoid amino acid epimerization.

The cleaving step (e2) may be carried out under acidic conditions, such as for example with trifluoroacetic acid (TFA), preferably at a dose between 1 to 100%, more preferably 10 to 100%, or acetic acid (AcOH), preferably at a dose between 10 to 100%.

Preferably, the reverse N to C peptide synthesis process according to the present invention comprises, before or after step (e2), a further step (f2) of deprotecting the amino acid lateral chains of the peptidic chains and/or COO-deprotecting the peptidic chains.

Moreover, the reverse N to C peptide synthesis processes according to the present invention may further comprise a final step of purifying the peptidic chains. The techniques used for purification are well known by the skilled person (high performance liquid chromatography (HPLC), etc. . . . ).

Examples of peptidic chains which can be obtained using the reverse N to C peptide synthesis process are COO-protected dipeptides H-Aib-Phe-OMe (Aib=amino-isobutyric acid, Phe=phenylalanine, Me=methyl) and H-Leu-Phe-OMe (Leu=leucine) (see part III.3 of the Examples and Synthesis scheme no 5 below).

In a further aspect, the invention relates to a C to N peptide synthesis process comprising the following successive steps:

(a3) coupling the solid phase-linker combination of formula (I) according to the present invention with N-protected and COO-protected amino acids whose lateral chains carry an unprotected group selected among an hydroxyl group, an amine group and a thiol group, in order to obtain N-protected and COO-protected amino acids coupled with the solid phase linker combination, (b3) N-deprotecting the COO-protected amino acids coupled to the solid phase linker combination in order to obtain N-deprotected COO-protected amino acid coupled to the solid phase linker combination, (c3) coupling the coupled N-deprotected COO-protected amino acids with N-protected amino acids in which the reactive functions of the amino acid lateral chains are protected in order to obtain N-protected COO-protected peptides coupled with the solid phase linker combination, (d3) N-deprotecting the coupled COO-protected peptides obtained in step (c3), (e3) optionally repeating steps (c3) and (d3) as many times as necessary in order to obtain a solid phase linker combination of formula (I) loaded with peptidic chains, (f3) cleaving the bond between the solid phase linker combination and the peptidic chains in order to recover the solid phase linker combination of formula (I) and peptidic chains.

The term "N-protecting group" as used in the present invention refers to the groups intended to protect an amino group against undesirable reactions during synthetic procedures. Commonly used N-protecting groups are disclosed in Greene, "Protective Groups In Organic Synthesis," (John Wiley & Sons, New York (1981)). N-protecting groups comprise carbamates, amides, N-alkyl derivatives, amino acetal derivatives, N-benzyl derivatives, imine derivatives, enamine derivatives and N-heteroatom derivatives. In particular, N-protecting groups include formyl, acetyl, benzoyl, pivaloyl, phenylsulfonyl, benzyl, t-butyloxycarbonyl (Boc), benzyloxycarbonyl (Cbz), trichloroethoxycarbonyl (Troc), allyloxycarbonyl (Alloc), fluorenylmethyloxycarbonyl (Fmoc), acetyl and the like.

Preferably, the N-protecting group of the N-protected amino acid is Fmoc and the N-deprotecting step is carried out with a dimethylformamide/piperidine solution.

Preferably, the coupling step (a3) and/or (c3) is carried out under O-(1H-benzotriazol-1-yl)-1,1,3,3-tetramethylphosphonium hexafluorophosphate activation in the presence of diisopropylethylamine in a solvent such as dimethylformamide.

Preferably, the C to N peptide synthesis process according to the present invention comprises before or after step (f3), a further step (g3) of deprotecting the amino acid lateral chains of the peptidic chains and/or COO-deprotecting the peptidic chains. The COO-deprotection of the peptidic chains may be carried out by saponification with a solution of LiOH in a solvent such as tetrahydrofurane.

Also preferably, the C to N peptide synthesis process is such that the N- and COO-protected amino acids whose lateral chains carry an unprotected group of step (a3) are selected from the group consisting of:

the N-protected and COO-protected threonine, serine and tyrosine which carry an hydroxyl group, the N-protected and COO-protected lysine, ornithine, diaminobutyric acid and diaminopropionic acid which carry an amine group, and the N-protected and COO-protected cysteine which carries a thiol group.

the N- and COO-protected amino acids tryptophan and arginin.

The COO-protected amino acid is as defined above. Advantageously, the COO-protecting group of the COO-protected amino acid is a $(C_1-C_6)$ alkyl group, advantageously a methyl.

Also advantageously, the N-protecting group of the N-protected amino acid is Fmoc and the N-deprotecting step is carried out with a dimethylformamide/piperidine solution.

The cleaving step (f3) may be carried out under acidic conditions, such as for example with trifluoroacetic acid (TFA), preferably at a dose between 1 to 100%, more preferably 10 to 100%, or acetic acid (AcOH), preferably at a dose between 10 to 100%.

Moreover, the C to N peptide synthesis processes according to the present invention may further comprise a final step of purifying the peptidic chains, the techniques employed for purification being well known by the skilled person.

Examples of peptidic chains which can be obtained using the C to N peptide synthesis process are N-protected and COO-protected dipeptides Fmoc-Ala-Ser-OMe (Ala=alanine, Ser=serine), Fmoc-Phe-Ser-OMe, Fmoc-Ala-Tyr-OMe (Tyr=tyrosine) and Fmoc-Phe-Tyr-OMe (see part III.5 of the Examples, Synthesis scheme no 7 below).

In a further aspect, the invention relates to a retro-inverso peptide synthesis process comprising the following successive steps:

(a4) coupling a compound of formula

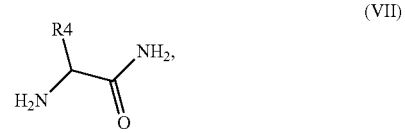

wherein $R_4$ represents the lateral chain of an amino acid in which the reactive functions are protected, with the solid phase linker combination of formula (I) according to the present invention in order to obtain a solid phase linker combination of formula

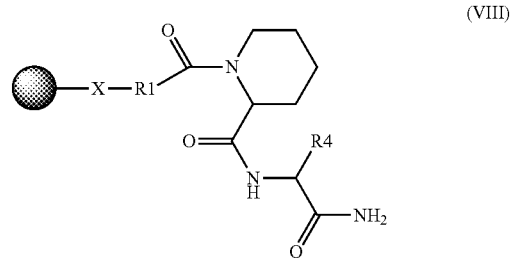

in which

X, $R_1$ and $R_4$ are as defined above, (b4) treating the solid phase linker combination of formula (VIII) obtained in step (a4) in order to obtain a solid phase linker combination of formula

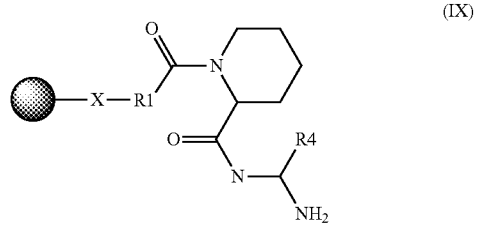

in which

X, $R_1$ and $R_4$ are as defined above, (c4) coupling the solid phase linker combination of formula (IX) obtained in step (b4) with N-protected amino-acids in which the reactive functions of the amino acid lateral chains are protected in order to obtain N-protected amino acids coupled to the solid phase linker combination of formula (IX), (d4) optionally N-deprotecting the coupled amino acids, (e4) optionally coupling the N-deprotected coupled amino acids of step (d4) with N-protected amino acids in which the reactive functions of the amino acid lateral chains are protected in order to obtain a N-protected peptide coupled with the solid phase linker combination of formula (IX), (f4) optionally repeating steps (d4) and (e4) as many times as necessary in order to obtain a solid phase linker combination of formula (I) loaded with retro-inverso peptidic chains, (g4) cleaving the bond between the solid phase linker combination and the peptidic chains in order to recover the solid phase linker combination of formula (I) and peptidic chains.

The N-protecting group is as defined above. Advantageously, the N-protecting group of the N-protected amino acid is Fmoc and the N-deprotecting step is carried out with a dimethylformamide/piperidine solution.

Preferably, the coupling step (a4) and/or (c4) and/or (e4) is carried out under O-(1H-benzotriazol-1-yl)-1,1,3,3-tetramethylphosphonium hexafluorophosphate activation in the presence of diisopropylethylamine in a solvent such as dimethylformamide.

Advantageously, the step (b4) is carried out by treatment with bistrifluoroacetoxy iodobenzene and pyridine in a solution such as a dimethylformamide/water solution.

Also advantageously, the retro-inverso peptide synthesis process according to the present invention comprises, before or after step (g4), a further step (h4) of deprotecting the amino acid lateral chains of the peptidic chains and/or N-deprotecting the peptidic chains.

The cleaving step (g4) may be carried out under acidic conditions, such as for example with trifluoroacetic acid (TFA), preferably at a dose between 1 to 100%, more preferably 10 to 100%, or acetic acid (AcOH), preferably at a dose between 10 to 100%.

Moreover, the retro-inverso peptide synthesis processes according to the present invention may further comprise a final step of purifying the peptidic chains.

An example of a retro-inverso peptidic chain which can obtained using the retro-inverso peptide synthesis process is N-protected pseudo-dipeptide Fmoc-Phe-g-DLeu-H (see part III.4 of the Synthesis scheme no 6 below).

The invention is further embodied in the following non-limiting examples and figures.

FIGURES

FIG. 1: Cleavage kinetics of the amide linkage, resin 2

Figure 2:
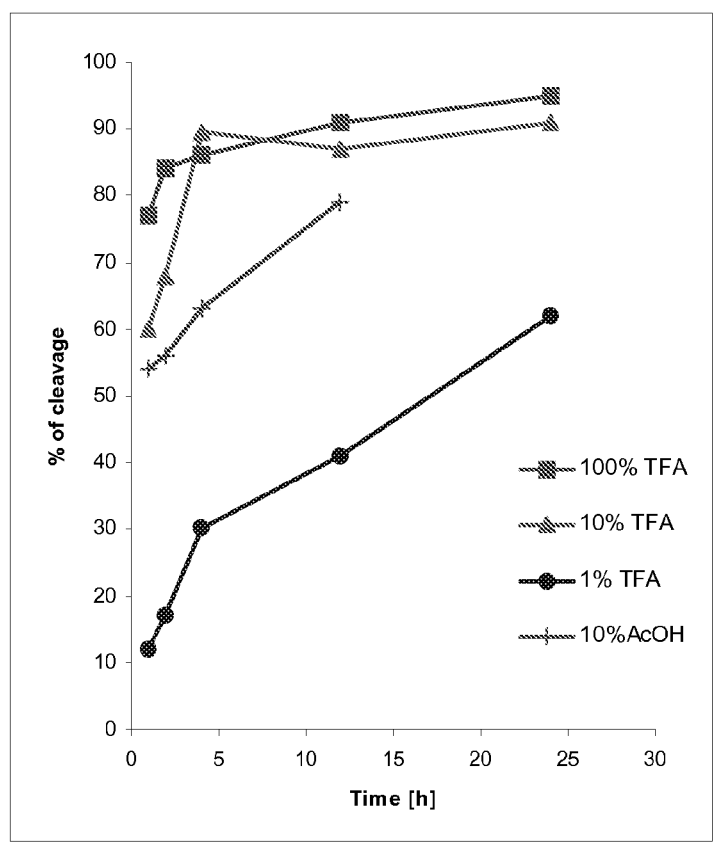

FIG. 2: Cleavage kinetics of the ester linkage resin 14 (Fmoc-Ser-OMe)

Figure 3:
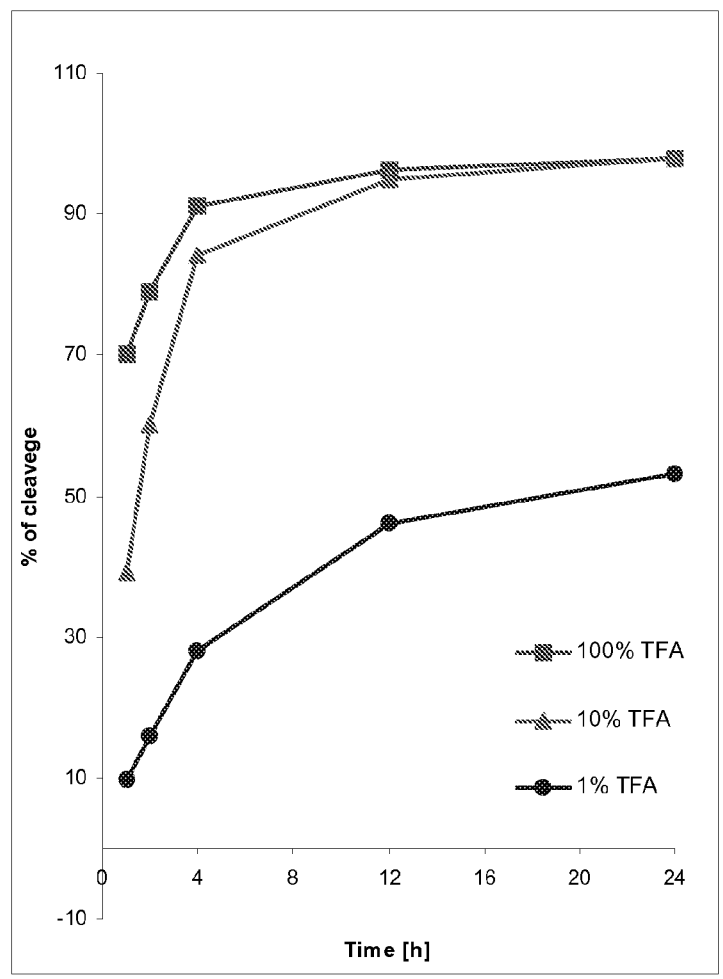

FIG. 3: Cleavage kinetics of the ester linkage resin 18 (Fmoc-Tyr-OMe)

EXAMPLES

In the present invention, the following abbreviations are used: AM-PS, aminomethyl polystyrene; BAL, Backbone Amide Linker; BOP, O-(1H-benzotriazol-1-yl)-1,1,3,3-tetramethylphosphonium hexafluorophosphate; BTIB, bis trifluoroacetoxy iodobenzene; DCM, dichloromethane; DIC, diisopropylocarbodiimide; DCC, dicyclohexylcarbodiimide; EDC, 1-Ethyl-3-(3-dimethylaminopropyl)carbodiimide; DIEA, diisopropylethylamine; DMF, dimethylformamide; PyBop, (Benzotriazol-1-yloxy)tripyrrolidinophosphonium hexafluorophosphate; PyBrop, Bromo-tris-pyrrolidino phosphoniumhexafluorophosphate; HBTU, O-Benzotriazole-N, N,N',N'-tetramethyl-uronium-hexafluoro-phosphate; HATU, N-[(dimethylamino)-1H-1,2,3-triazolo-[4,5-b]pyridine-1-yl-methylene]-N-methylmethanaminium hexafluorophosphate N-oxide; HMBA, Hydroxymethyl benzamido linker; HOBT, hydroxybenzotriazole; HOAt, 1-Hydroxy-7-azabenzotriazole, HPLC, High Performance Liquid Chromatography; LC/MS, Tandem Liquid Chromatography/Mass Spectroscopy; Pip, pipecolic linker; PS, polystyrene; SPPS, Solid Phase Peptide Synthesis; TEA, triethylamine; NMM, N-methyl morpholine; TFA, trifluoroacetic acid; THF, Tetrahydrofurane; TIS, triisopropylsilane; TMP, 2,4,6 trimethylpyridine; TNBS, trinitrobenzenesulfonic acid. Other abbreviations used were those recommended by the IUPAC-IUB Commission (Eur. J. Biochem. 1984, 138, 9-37).

Commercially available aminomethyl-PS resin cross linked with 1% DVB, 100-200 mesh, loading 1.3 mmol/g was purchased from Senn Chemicals. The activation reagents were from Senn other reagents from Acros and Lancaster. Aminoacids derivatives were from Iris Biotech.

All the stages of linker preparation were monitored by colorimetric tests. Additionally IR spectra were performed on the resin beads.

In the following examples, the pipecolic linker (Pip) which is used contains $R_1$=cyclohexyl.

I—Preparation of the Pipecolic Linker Solid Support

The preparation of the pipecolic linker solid support is as disclosed in the following synthesis scheme no 1:

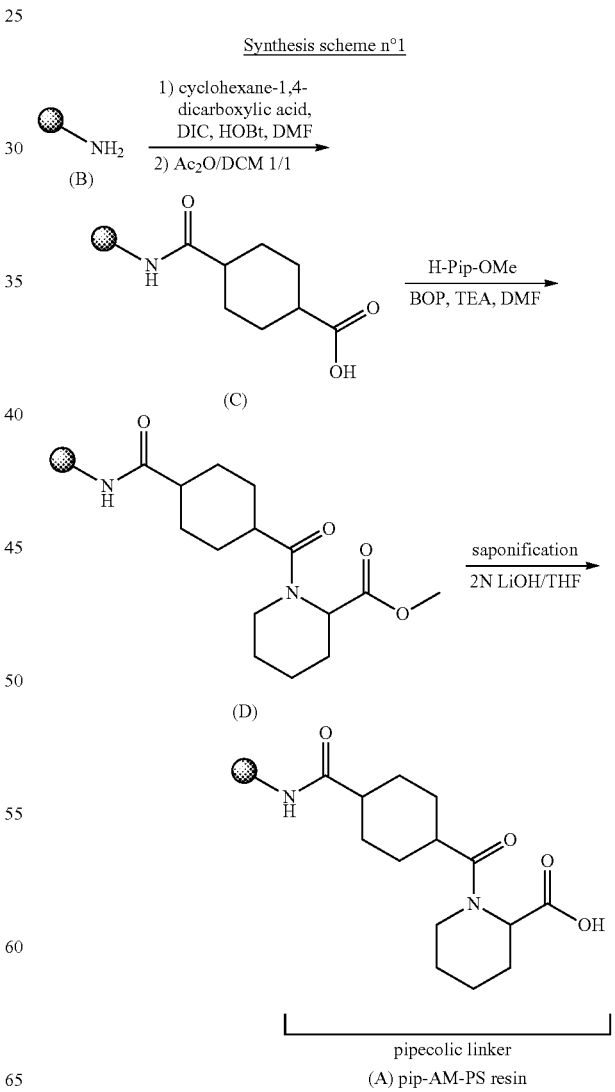

Cyclohexane-1,4-dicarboxylic acid was used as a spacer between amino methyl polystyrene resin and a pipecolic acid. Cyclohexane-1,4-dicarboxylic acid was coupled to the aminomethyl polystyrene resin (B) (theoretical loading: 1.2 mmol/g) using diisopropylcarbodiimide (DIC) and hydroxybenzotriazole (HOBt) as a coupling mixture in dimethylformamide (DMF) for 12 h. The effectiveness of acylation was monitored by Kaiser and TNBS tests. After capping unreacted amino functions by using acetic anhydride, pipecolic acid methyl ester was anchored to the solid support (C). Reaction was performed under BOP-promoted amide coupling in the presence of triethylamine (TEA) in DMF for 2 h.

The acylation was repeated once more for one hour, and the lack of free carboxylic acid function was confirmed by the malachite green test (Attardi et al., 2000). The resin (D) obtained was then hydrolyzed by using the protocol previously optimized in the laboratory (Cantel et al., 2003) to yield pipecolic aminomethyl polystyrene resin namely pip-AM-PS (A). The methyl ester hydrolysis on solid support involves treatment of the resin with a 2N solution of LiOH in tetrahydrofuran (THF) (Cantel et al., 2004).

The presence of the new handle attached to the resin was additionally verified by using IR spectrometry (spectra not shown). The first assay was performed with regular aminomethylated PS resin (red) and then with pipecolic linker derived PS resin (black). Spectrum of the starting resin consisted of peaks originating mainly from polystyrene peaks appearing between 3058 and 2857 cm$^{-1}$ that represent CH, CH$_2$ stretching modes. The amino group gave rise to the band at ca. 3400-3327 cm$^{-1}$ originating from free primary amino function. Although the latter band range was characteristic of free hydroxyl groups of carboxylic functions of pipecolic acid, in the spectra of the pipecolic resin the band at ca. 1717-1700 cm$^{-1}$ was attributed to the carbonyl group of the carboxylic acid function. Moreover, the carbonyl groups originating from amide groups could be observed at 1641 cm$^{-1}$. Interestingly, in the spectra of the pipecolic linker functionalized PS resin a disappearance of the NH band at 1602 cm$^{-1}$ was observed.

Attachment of cyclohexane 1,4-dicarboxylic acid

Cyclohexane 1,4-dicarboxylic acid (30.0 mmol, 5 eq) and HOBt (30.0 mmol, 5 eq) were dissolved in 20 mL of DMF, then DIC (30.0 mmol, 5 eq) were added and the mixture was gently stirred for 10 min. It was then added to 5 g of aminoethyl-PS resin ((B), which corresponds to the functionalized solid support of formula (V), wherein preX is NH$_2$) (1.3 mmol/g) was pre-swollen in DCM, and the reaction mixture was gently shacken for 6 hours. After filtration, the resin was washed with DMF, MeOH, and DCM, and dried at room temperature under vaccuo. The coupling efficiency was checked by Kaiser and TNBS tests. Finally, the resin was treated with a mixture of Ac$_2$O/DCM (50/50. v/v) and washed three times with DCM to yield resin ((C), corresponding to the compound of formula (III) wherein X=—NH—CO— and R$_1$=cyclohexyl).

Attachment of Pipecolic Acid Methyl Ester

Pipecolic acid methyl ester hydrochloride (2.33 g, 2 eq) was coupled to the resin using BOP (12 mmol, 2 eq) and HOBt (12 mmol, 2 eq), as activating agents in the presence of DIEA (30 mmol, 5 eq). The reaction mixture was allowed to react for 2 hours, and the process was repeated once more. Finally, the resin was washed with DMF, MeOH, and DCM to yield resin ((D), corresponding to the compound of formula (II) wherein X=—NH—CO—, R$_1$=cyclohexyl and R$_3$=methyl).

Hydrolysis of Pipecolic Acid Methyl Ester

The methyl ester of the resin bound pipecolic derivative (D) was hydrolyzed in a mixture of 2 M aqueous solution of lithium hydroxide and tetrahydrofuran 30/70 (v/v) during 12 hours at room temperature. The resin (D) was washed with H$_2$O, MeOH, DCM to yield pipecolic AM PS resin ((A), corresponding to the compound of formula (I) wherein X=—NH—CO— and R$_1$=cyclohexyl) calculated loading of 0.91 mmol/g.

II—Example of 'on Resin' Methyl Ester Hydrolysis

Pip-AM-PS resin-bound aminoacid methyl ester (1 g) was treated with 5 mL of a mixture of 2M aqueous solution of LiOH and tetrahydrofuran (30/70, v/v). The reactor was shacked at room temperature for 12 hours, and the resin was washed with H$_2$O (3×), THF (3×), MeOH (3×), DCM (2×), and finally dried under vacuum.

III—Application Studies

The following synthesis scheme no 2 discloses general use of the pipecolic linker solid support (A) wherein the solid support is a polystyrene support, X is —NH—CO— and R$_1$ is cyclohexyl:

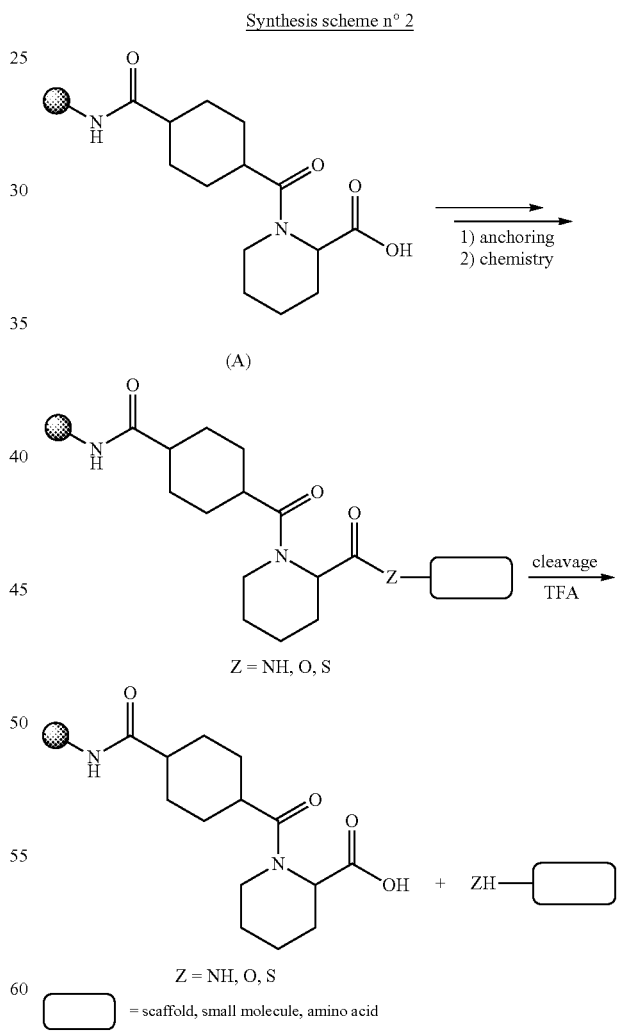

III.1 Initial Loading Determination

Before performing loading experiments with pip-AM-PS resin (A), the Inventors determined the experimental loading of the aminomethyl resin used for pipecolic linker preparation:

Synthesis scheme n°3

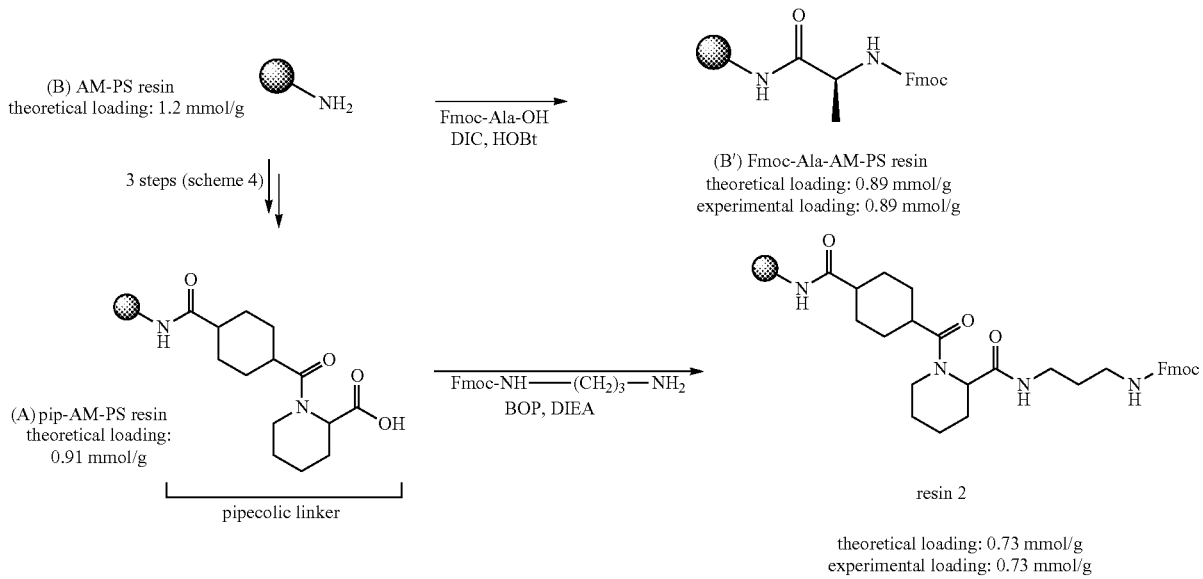

Fmoc-Ala-OH was readily coupled to the commercial aminomethyl polystyrene resin (AM-PS resin (B), theoretical loading=1.2 mmol/g). The reaction was performed by double coupling using diisopropylocarbodiimide (DIC) and hydroxybenzotriazole (HOBt) in DMF. The effectiveness of acylation was confirmed by negative Kaiser and TNBS tests. Maximum theoretical loading of Fmoc-Ala-AM-PS resin was calculated on a basis of theoretical mass increment induced by Fmoc-Ala-OH coupling, according to the equation: 1.2/[1+(1.2×0.294)]=0.89 mmol/g. Experimental loading was determined by the mean of three successive UV titration of released dibenzofulvene upon Fmoc cleavage from Fmoc-Ala-AM-PS resin (mass increment=294 g/mol), according to the standard protocol for resin loading determination. This experimental value is equal to the theoretical value of 0.89 mmol/g (Table 1).

The same kind of experiment was performed to determine the loading of pip-AM-PS resin (A) prepared on AM-PS resin (B) according to the protocol described in Synthesis scheme no 1 (part I of the Examples). Fmoc-1-amino-3-aminopropane was coupled to the pipecolic resin (A) using BOP activation in the presence of DIEA in DMF for two hours. Effectiveness of the coupling reaction was verified by the malachite green colorimetric test (Attardi et al., 2000), checking the disappearance of carboxylic acid functions on resin beads. Theoretical loading of resin 2, including molecular weight of pipecolic linker and Fmoc-1-amino-3-aminopropane (mass increment=544 g/mol), was calculated on a basis of equation: 1.2/[1+(1.2×0.544)]=0.73 mmol/g. Loading was determined on resin 2 by Fmoc titration yielding a value of 0.73 mmol/g, indicating that the linker synthesis and the amine anchoring was quantitative.

According to loading determination experiments, preparation of the pipecolic linker is quantitative. It is possible to calculate loading of pip-AM-PS resin (A) according to the mass increment of pipecolic linker (266 g/mol) starting from the AM-PS resin (1.2 mmol/g) 1.2/[1+(1.2×0.266)]=0.91 mmol/g.

TABLE 1

Loading determination (Fmoc titration)

| Resin | Exp. Loading (Fmoc titration) (mmol/g) | Mass increment[a] (mg/mol) | Theoretical loading (mmol/g) [b] |
|---|---|---|---|
| AM-PS resin (D) | NA | NA | 1.2 |
| Fmoc-Ala-AM-PS resin | 0.89 | 0.294 | 0.89 |
| Resin 2 | 0.73 | 0.544 | 0.73 |
| Pip-AM-PS resin (A) | NA | 0.266 | 0.91 |

[a] Calculated starting from AM PS resin, loading 1.2 mmol/g
[b] Calculated by the equation: 1.2/[1 + (1.2 × Mass increment)]

III.2 Amine Anchoring

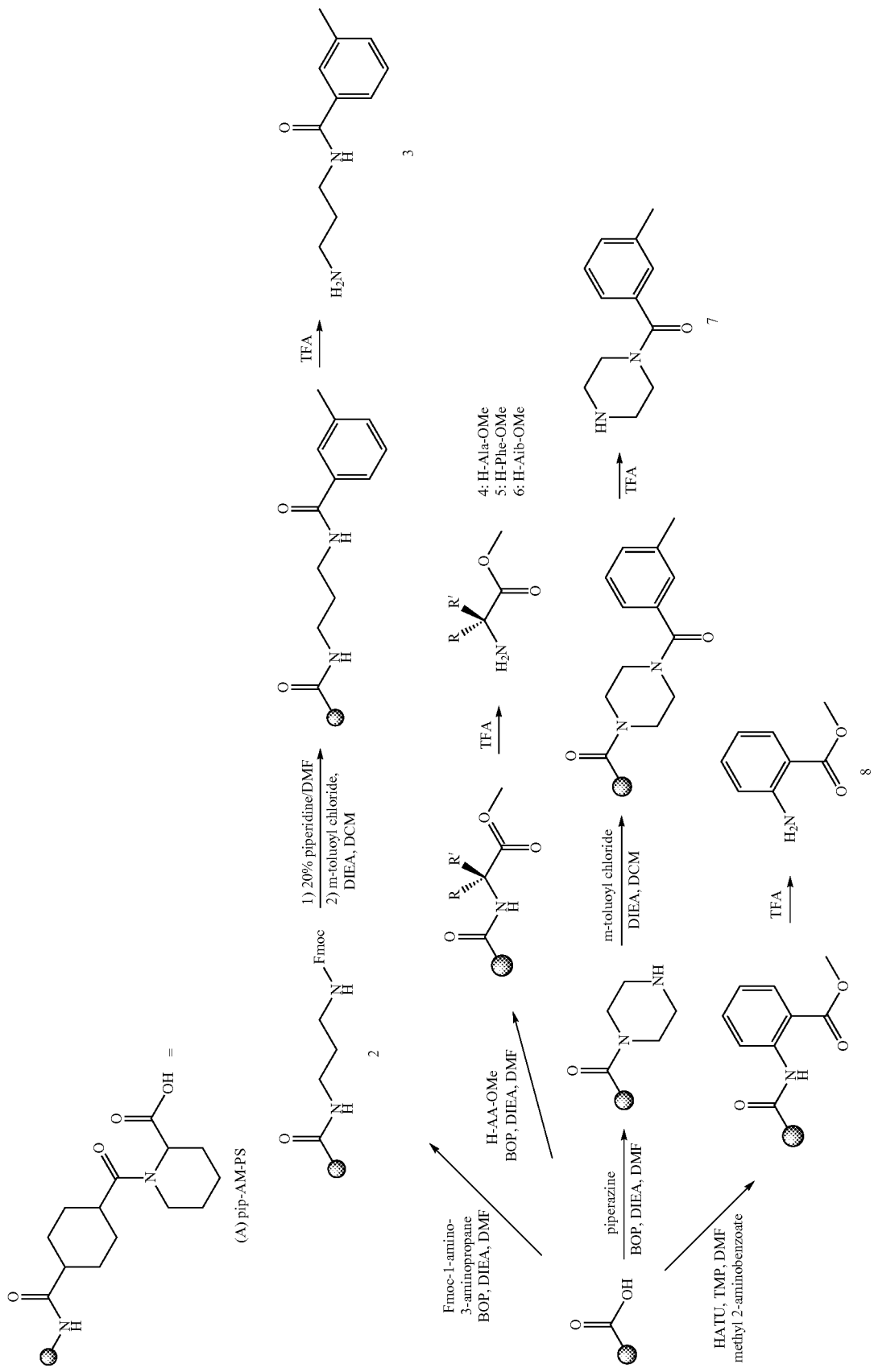
Synthesis scheme n°4: Anchoring of model amines on pipecolic linker

As pipecolic linker was first designed to anchor various amine or alcohol building blocks by creation of amide or ester linkage respectively, several assays were performed to check its versatility. First, the attempts to anchor several model amines to the support and their subsequent modifications in experimental conditions stable for the linker, by using several coupling reagents, were undertaken. Fmoc-1-amino-3-aminopropane was chosen as a model primary amine, piperazine as a model secondary amine, methyl 2-amino benzoate as a model aromatic amine. Moreover, amino acid methyl esters of Alanine, Phenylalanine, and Aminoisobutyric acid were also used to prove the usefulness of pipecolic linker in the field of peptide chemistry. Purity of the released compounds upon 90 minutes-TFA cleavage was determined on by the relative area of integrated peaks of HPLC analysis (sum of absorbance between 200 and 270 nm). Yields were determined by weighing the products released from the resin (Table 2 below).

Example 1

Attachment of Primary Amine (H-Phe-Ome) to the PIP-AM-PS Resin and Recovery of this Primary Amine Pipecolic AM-PS resin (A) (200 mg, 0.182 mmol, 0.91 mmol/g), was swollen in 5.4 mL of DMF coupling solution containing BOP (239 mg, 100 mM, 540 μmol, 3 eq), DIEA (140 mg, 188 μl, 200 mM, 1.08 mmol, 6 eq), and H-Phe-OMe (97 mg, 100 mM, 540 μmol, 3 eq). The resin was gently stirred for 2 hours and then washed with DMF (3×), MeOH, DCM (2×). The resin was cleaved with TFA during 90 minutes under gentle stirring. Resin was filtered and the TFA solution evaporated under nitrogen. The residue was dissolved in acetonitrile/water 1/1 solution and freeze dried. After lyophilisation, 25.6 mg (yield 48%, purity 98%) of compound 5 as TFA salt, were obtained and submitted to LC/MS and HPLC analysis (RT=0.70 min, MS ESI+[M+H]$^+$ m/z=180.3).

Example 2

Attachment of Aromatic Amine (Methyl 2-Aminobenzoate) to the PIP-AM-PS Resin and Recovery of this Aromatic Amine Pipecolic AM-PS resin (A) (200 mg, 0.182 mmol, 0.91 mmol/g), was swollen in 5.4 mL of DMF coupling solution containing HATU (276 mg, 135 mM, 730 μmol, 4 eq), TMP (177 mg, 194 μl, 270 mM, 1.46 mmol, 8 eq), and methyl 2-aminobenzoate (81 mg, 69 μl, 135 mM, 730 μmol, 4 eq).

The resin was gently stirred for 2 hours and then washed with DMF (3×), MeOH, DCM (2×). The resin was cleaved with TFA during 90 minutes under gentle stirring. Resin was filtered and the TFA solution evaporated under nitrogen. The residue was dissolved in acetonitrile/water 1/1 solution and freeze dried. After lyophilisation, 22.6 mg (yield 47%, purity 97%) of compound 8 as TFA salt, were obtained and submitted to LC/MS and HPLC analysis (RT=0.72 min, MS ESI+[M+H]$^+$ m/z=152.3).

Example 3

Preparation of Compound 7, Piperazin-1-yl M-Tolyl Methanone

Pipecolic AM-PS resin (A) (100 mg, 91 μmol, 0.91 mmol/g), was swollen in 2.7 mL of DMF coupling solution containing BOP (119 mg, 100 mM, 270 μmol, 3 eq), DIEA (70 mg, 94 μl, 200 mM, 540 μmol, 6 eq), and piperazine (21 μl, 23 mg, 100 mM, 270 μmol, 3 eq). The resin was gently stirred for 2 hours and then washed with DMF (3×), MeOH, DCM (2×) to yield solid supported piperazine. Then, the resin was gently shaken for 2 hours in 2.7 mL of DCM solution containing m-toluoyl chloride (56 mg, 48 μl, 135 mM, 365 μmol, 4 eq) and DIEA (127 μl, 94 mg, 270 mM, 730 μmol, 8 eq). Resin was washed with DMF (3×), MeOH, DCM (2×) and cleaved with TFA during 90 minutes under gentle stirring. Resin was filtered and the TFA solution concentrated under nitrogen. The residue was dissolved in acetonitrile/water 1/1 solution and freeze dried. After lyophilisation, 11.8 mg (yield 41%, purity 98%) of compound 7 were obtained as TFA salt and submitted to LC/MS and HPLC analysis (RT=0.54 min, MS ESI+[M+H]$^+$ m/z=205.1)

TABLE 2

Pipecolic Linker cleavage results

| Cpds | $R_t$ | Purity %[a] | [M + H]$^+$ found | MW calc. | Yield[b] |
|---|---|---|---|---|---|
| 3 | 0.52 | 99% | 193.4 | 192.1 | 66.00 |
| 4 | 0.34' | 99%[c] | 104.2 | 103.1 | 38.00 |
| 5 | 0.70 | 98% | 180.3 | 179.1 | 48.00 |
| 6 | 0.36[c] | 99%[c] | 118.3 | 117.1 | 34.00 |
| 7 | 0.54 | 98% | 205.1 | 204.1 | 41.00 |
| 8 | 0.72 | 97% | 152.3 | 151.1 | 47.00 |
| 9 | 0.70 | 95% | 265.1 | 264.1 | 41.00 |
| 10 | 0.89/0.98[d] | 96% | 293.3 | 292.2 | 46.00 |
| 11 | 1.52 | 92% | 472.6 | 471.3 | 46.00 |
| 13 | 1.41 | 98% | 356.2 | 355.1 | 19.00 |
| 15 | 1.35 | 97% | 342.0 | 341.1 | 30.00 |
| 16 | 1.26 | 96% | 412.9 | 412.2 | 19.00 |
| 17 | 1.48/1.56[d] | 86% | 489.6 | 488.2 | 17.00 |
| 19 | 1.55 | 98% | 418.6 | 417.2 | 25.90 |
| 20 | 1.47 | 97% | 489.6 | 488.2 | 14.00 |
| 21 | 1.69 | 94% | 565.6 | 564.2 | 13.00 |

[a]Purity percent is calculated on the peak area integration during HPLC analysis of cleaved compounds at sum of wavelengths between 200 to 270 nm.
[b]Yield is calculated by weighting the cleaved products on the basis of experimental loading determined on resin (A) (0.91 mmol/g).
[c]Standard UV detection is impossible for this compound. Purity percent and retention time are calculated on the peak area integration of TIC chromatogram during LC/MS analysis.
[d]Two isomers somers diastereoisomers were observed by HPLC analysis.

Secondary and primary amines, including amino acid methyl esters were easily coupled to the support using BOP activation in the presence of DIEA in DMF with modest to good yields. The purity of the released compounds was pretty high. In the case of model primary aromatic amine, methyl 2-amino benzoate, moderate yields were obtained with such activation (12% yield). The Inventors investigate other coupling reagents. The most efficient method was found to be N-[(dimethylamino)-1H-1,2,3-triazolo-[4,5-b]pyridine-1-yl-methylene]-N-methylmethanaminium hexafluorophosphate N-oxide (HATU) activation in the presence of 2,4,6 trimethylpyridine (TMP) in dimethylformamide, improving yield to 51% (purity 99%).

It is worth noting that using pipecolic linker, the bulky α-amino-isobutyric acid methyl ester (H-Aib-OMe) was successfully attached to the support under simple BOP activation (compound 6) with a yield of 34%. More generally, use of pipecolic linker significantly improved resin anchoring of amines compared to trityl linkers. As an example, starting from 2-chloro chlorotrityl PS resin (1.6 mmol/g) (Barlos et al., 1988; Bernhardt et al., 1997), the loading of the primary amine of the amino acid side chain (Orn, Lys) was less than 0.3 mmol/g.

III.3 Application to Reverse N to C Peptide Synthesis

The following synthesis scheme no 5 discloses the reverse N to C SPPS on pipecolic solid support:

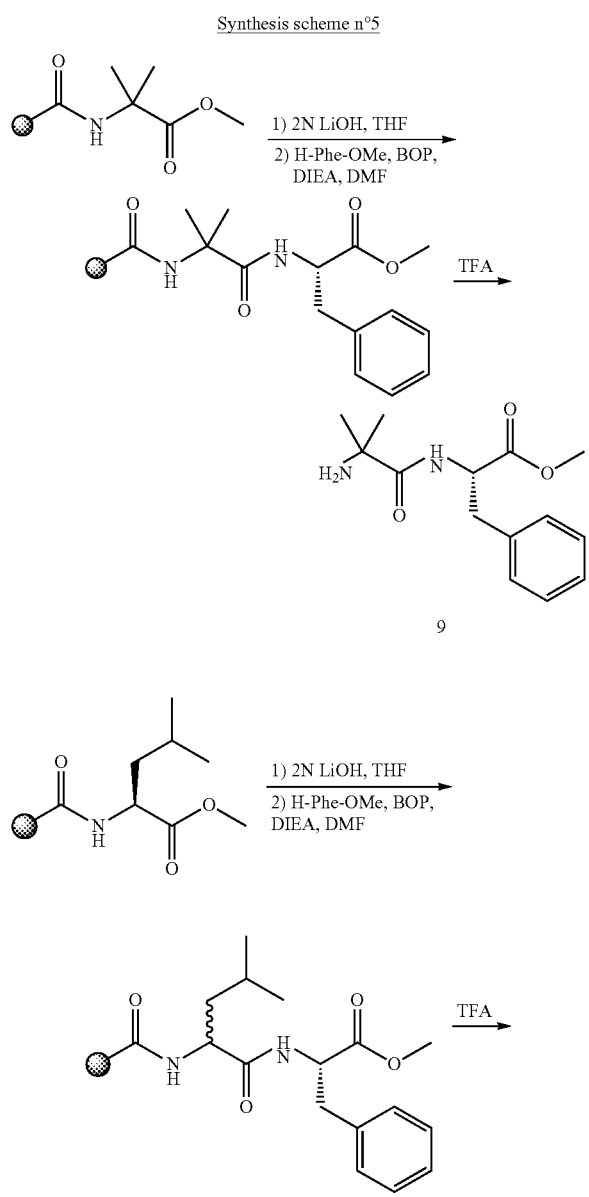

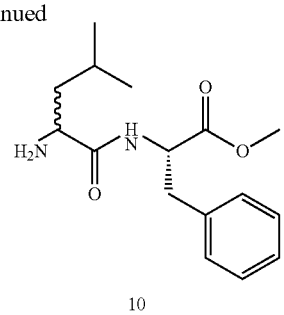

The Inventors investigated the possibility of application of pipecolic linker for the N to C reverse solid-phase peptide synthesis. To perform this approach pipecolic linker should be stable during the C-terminal protection removal. To check this important aspect, solid supported Aib and Leu methyl esters were submitted to saponification with 2N LiOH in THF and then coupled to H-Phe-OMe using the previously described standard BOP/DIEA activation protocol. Routinely, the effectiveness of the coupling reactions was verified by using the malachite green colorimetric test.

Dipeptides 9 and 10, respectively H-Aib-Phe-OMe and H-Leu-Phe-OMe, were obtained with good yields and purities after TFA treatment for 90 minutes (Table 2). As expected, elongation of the amino acid chain from N- to C-terminus resulted in the lost of the chiral integrity of the dipeptide 10. Indeed, Leucine residue attached to the support was easily epimerized by oxazolonium ion formation through the attack of the oxygen from the pipecolic handle-amide bond onto the activated carboxylic acid function. Thus, in the case of coupling of resin-bound Leucine to H-Phe-OMe using BOP/DIEA activation, a total epimerization had occurred (50/50) as shown by HPLC analysis. It is worth noting that the epimerization phenomenon during reverse SPPS activation has been previously investigated by other authors. It was found that either coupling protocol or the coupling reagents influence the epimerization rate. Although the purpose of the present study was not to determine a non-racemizing method, the Inventors used HATU in the presence of TMP in DMF, conditions that were already described to minimize racemization (Gutheil, W. G.; Xu, Q. In *PCT Int. Appl.*; (The Curators of the University of Missouri, USA). Wo, 2002, p 30 pp; Johansson, A.; Akerblom, E.; Ersmark, K.; Lindeberg, G.; Hallberg, A. *Journal of Combinatorial Chemistry* 2000, 2, 496-507). In this case, the epimerization rate was below 10% according to HPLC analysis of the dipeptide H-Leu-Phe-OMe.

III.4 Pseudopeptide Chemistry: Synthesis of Gem Diamino Derivatives on Solid Support The following synthesis scheme no 6 discloses synthesis of Fmoc-Phe-g-DLeu-H using the pipecolic solid support:

Synthesis scheme n°6

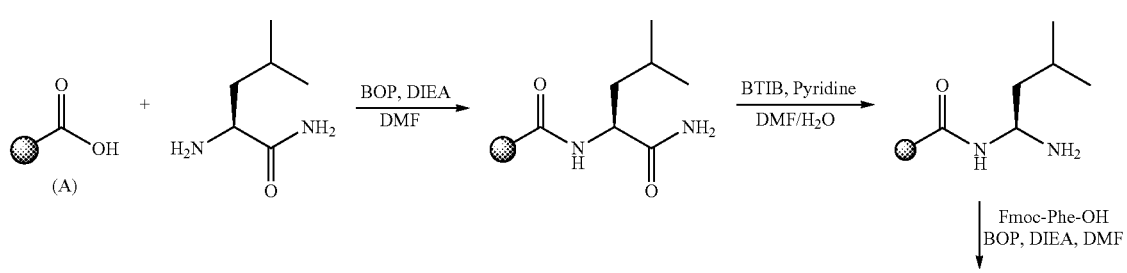

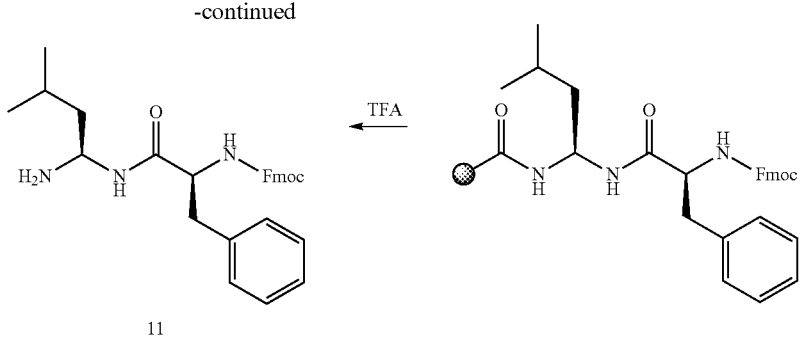

The pipecolic linker strategy was also applied to the solid phase synthesis of gem-diamino derivatives according to the general concept involving Hoffman rearrangement. Adaptation of this strategy to solid supported chemistry is of high interest because it allows synthesizing retro-inverso or retro peptides in an easy way, avoiding the tedious preparation of unstable gem-diamino derivatives in solution (Cantel et al., 2003). For this purpose the Inventors decided to synthesize the pseudo-dipeptide 11, Fmoc-Phe-g-DLeu-H.

H-Leu-NH$_2$ was coupled to the pipecolic handle through standard BOP/DIEA activation. Treatment with BTIB (bis-trifluoroacetoxy iodobenzene) and pyridine in DMF/water solution afforded the gem diamino acid derivative of Leucine anchored on solid support thought an amide bond. Next, coupling with Fmoc-Phe-OH gave the pseudodipeptide anchored to the solid support. TFA-mediated cleavage released the pseudo-dipeptide 11 (Fmoc-Phe-g-DLeu-H) with 46% yield and 92% purity. This strategy opens a new way of synthesis of retroinverso and inverso peptides, greatly facilitating the on-support generation and handling of gem diaminoacids. The same sequence was investigated to generate Fmoc-Phe-g-Aib-H. Only 50% purity was observed, due to the difficulty of undergoing Hoffman rearrangement on hindered amino acid such as Aib.

Example 4

Preparation of the Gem-Diamino Derivative 11, Fmoc-Phe-G-Dleu-H on PIP-AM-PS Resin Pipecolic AM-PS resin (A) (250 mg, 225 μmol, 0.91 mmol/g), was swollen in 6.75 mL of DMF coupling solution containing BOP (298 mg, 100 mM, 675 μmol, 3 eq), DIEA (236 mg, 317 μl, 200 mM, 1.82 mmol, 6 eq), and H-Leu-NH$_2$ (88 mg, 100 mM, 675 μmol, 3 eq). The resin was gently stirred for 2 hours and then washed with DMF (3×), MeOH, DCM (2×). The resin was then swollen in 5 mL of DMF/H$_2$O (80/20, v/v) solution containing pyridine (147 μl, 144 mg, 365 mM, 1.82 mmol, 8.1 eq) and BTIB (157 mg, 73 mM, 365 μmol, 1.62 eq) and was stirred for 1 h. The resin was then washed with DMF (3×) and DCM (2×). The resin obtained was swollen in 6 mL of DMF coupling solution containing BOP (398 mg, 150 mM, 0.9 mmol, 3 eq), DIEA (233 mg, 314 μl, 300 mM, 1.8 mmol, 6 eq) and Fmoc-Phe-OH (349 mg, 150 mM, 0.9 mmol, 3 eq). The resin was gently stirred for 2 hours and then washed with DMF (3×), MeOH and DCM (2×). Resin was finally cleaved with TFA during 90 minutes under gentle stirring. Resin was filtered and the TFA solution concentrated under nitrogen. The residue was dissolved in acetonitrile/water 1/1 solution and freeze dried. After lyophilisation, 60 mg (yield 46%, purity 92%) of compound 11 were obtained as TFA salt and submitted to LC/MS and HPLC analysis (RT=1.52 min, MS ESI+[M+H]$^+$ m/z=472.6).

III.5 Alcohol Anchoring

Regarding the simple reaction sequence that was performed for attachment of the amine building blocks to the pipecolic handle, the Inventors stated that similar reaction conditions might be used for introduction of an alcohol derivative through an ester linkage. As a proof of concept, they chose amino acids side chains to perform the attachment to the linker. The primary alcohol function of Serine side chain, secondary alcohol of Threonine and phenolic function of Tyrosine were used in these assays.

TABLE 3

Loading determination after alcohol side chain anchoring (Fmoc titration)

| Resin | Exp. Loading (Fmoc titration) (mmol/g) | Mass increment[a] (mg/mol) | Theoretical loading (mmol/g)[b] |
|---|---|---|---|
| 12 (Side Chain Thr) | 0.30 | 0.604 | 0.69 |
| 14 (Side Chain Ser) | 0.32 | 0.590 | 0.70 |
| 18 (Side Chain Tyr) | 0.43 | 0.666 | 0.67 |

[a]Calculated starting from AM PS resin, loading 1.2 mmol/g
[b]Calculated by the equation: 1.2/[1 + (1.2 × Mass increment)]

Apart from demonstrating the possibility of alcohol immobilization on pipecolic linker, this side-chain anchoring strategy could also be of interest to generate cyclic peptides or to yield C-terminus modified peptides, using Fmoc or Alloc-chemistry. A cycle of deprotection/coupling step was performed on side chain-grafted amino acid to check this approach. The following synthesis scheme no 7 discloses the anchoring of model alcohols on pipecolic linker solid support: side chains of Thr, Ser and Tyr.

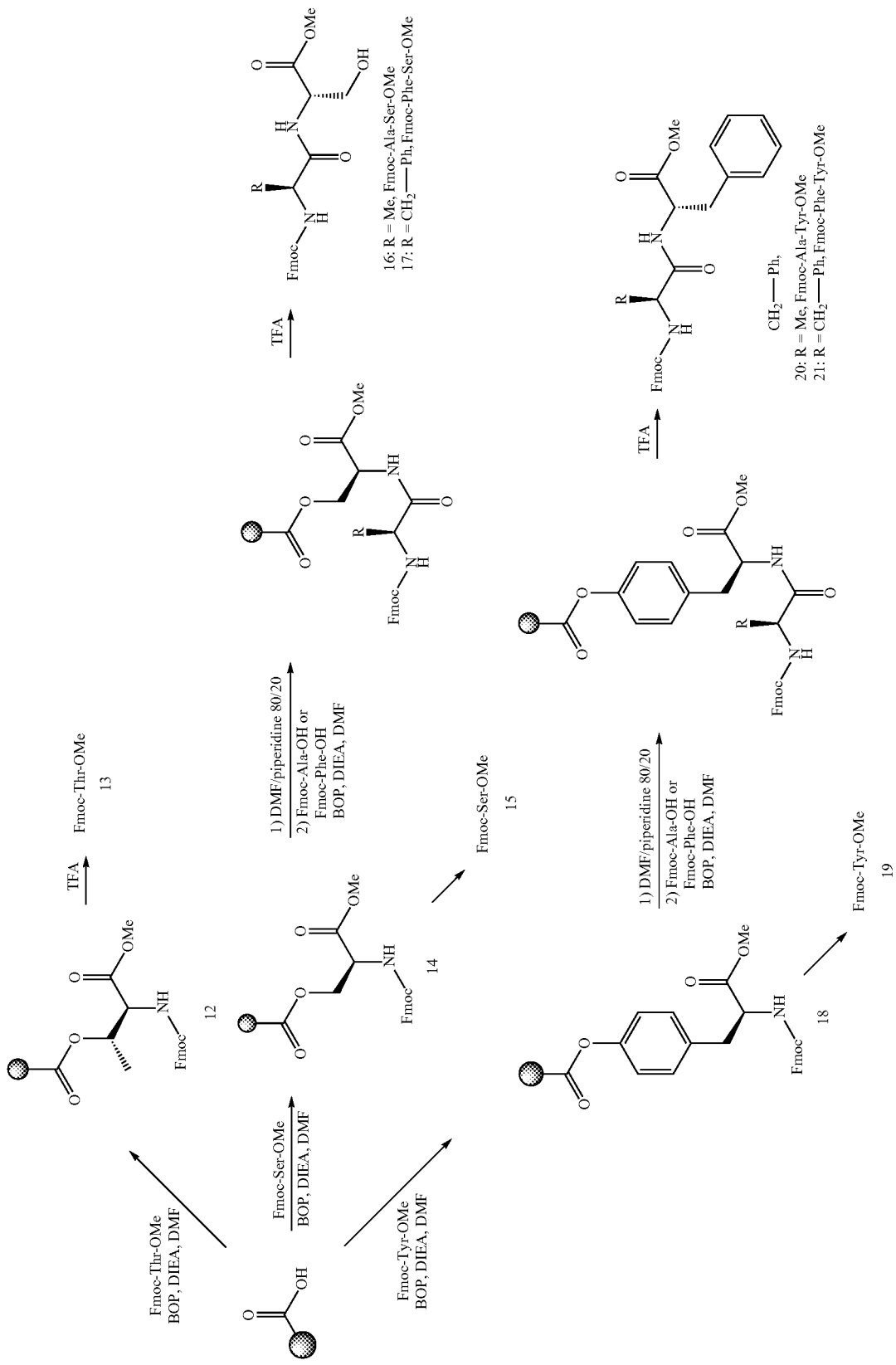

Ester bond between the pipecolic handle and side chain of amino acids was formed by using BOP/DIEA coupling for 90 minutes. Loading was determined by Fmoc titration on aliquots of resins 12, 14 and 18 for Thr, Ser and Tyr-functionalized resins, respectively (Table 3). Surprisingly, use of DIC/ DMAP activation didn't give better result than BOP/DIEA mediated esterification. In a general manner, alcohol immobilization was less efficient than amine loading, according to Fmoc titration results, even when a negative malachite green test was observed. In particular with resins 12 and 14, obtained by the esterification of Fmoc-Thr-OMe and Fmoc-Ser-OMe side chains, experimental loadings were only 0.30 mmol/g and 0.32 mmol/g (i.e. 43% and 44% yield compared to maximum theoretical loading of 0.70 mmol/g). This result has to be put in perspective with the difficulty of loading primary alcohols on trityl-based resins giving experimental loading yields lower than 20% when compared to theoretical maximum loading (Barlos et al., 1988).

After loading determination, they decided to check the possibility of continuing Fmoc SPPS on side chain anchored Fmoc amino acids. For this purpose, resins 14 and 18 were submitted to Fmoc deprotection for 20 minutes in DMF/pip 8/2 solution, then underwent coupling step with either Fmoc-Phe-OH or Fmoc-Ala-OH using BOP/DIEA activation. Subsequently, dipeptides 16, 17, 20, 21 (Fmoc-Phe-Ser-(OH)-OMe, Fmoc-Ala-Ser-(OH)-OMe, Fmoc-Phe-Tyr(OH)-OMe, Fmoc-Ala-Tyr(OH)-OMe, respectively) were successfully cleaved from the solid-support by the treatment with TFA with high purities and 15% yields.

A diastereoisomer of dipeptide 17 (Fmoc-Phe-Ser-OMe) was identified (<10%), probably due to enolization promoted by epimerization of the serine residue during coupling of Fmoc-Ser-OMe on the pipecolic linker. Serine is well known for its sensitivity towards epimerization. In the case of the tyrosine-bound to the solid-support no epimerization was observed.

Example 5

Attachment of Alcohol (Fmoc-Ser-Ome) to the PIP-AM-PS Resin and Recovery of this Alcohol Pipecolic AM-PS resin (A) (200 mg, 0.182 mmol, 0.91 mmol/g), was swollen in 5.4 mL of DMF coupling solution containing BOP (239 mg, 100 mM, 540 µmol, 3 eq), DIEA (140 mg, 188 µl, 200 mM, 540 µmol, 6 eq) and Fmoc-Ser-OMe (184 mg, 100 mM, 540 µmol, 3 eq). The resin was gently stirred for 2 hours and then washed with DMF (3×), MeOH, DCM (2×). The resin 14 was cleaved with TFA during 90 minutes under gentle stirring. Resin was filtered and the TFA solution concentrated under nitrogen. The residue was dissolved in acetonitrile/water 1/1 solution and freeze dried. After lyophilisation, 18.2 mg (yield 30%, purity 97%) of compound 15 were obtained and submitted to LC/MS and HPLC analysis (RT=1.35 min, MS ESI+[M+H]$^+$ m/z=342.0)

Example 6

Acylation of Amino Acid Bound to the Linker by Lateral Chain: C to N Dipeptide Synthesis Resin 14 (i.e. Fmoc-Ser(pip-AM-PS resin)-OMe) (100 mg, 32 µmol, 0.32 mmol/g), was swollen in 2.7 mL of DMF coupling solution containing BOP (119 mg, 100 mM, 270 µmol, 8.4 eq), DIEA (70 mg, 94 µl, 200 mM, 540 µmol, 16.8 eq), and Fmoc-Ala-OH (84 mg, 100 mM, 270 µmol, 8.4 eq). The resin was gently stirred for 2 hours and then washed with DMF (3×), MeOH, DCM (2×) and cleaved with TFA during 90 minutes under gentle stirring. Resin was filtered and the TFA solution concentrated under nitrogen. The residue was dissolved in acetonitrile/water 1/1 solution and freeze dried. After lyophilisation, 8.4 mg (acylation step yield: 64%, total yield: 19%, purity 96%) of dipeptide 16 were obtained and submitted to LC/MS and HPLC analysis (RT=1.26 min, MS ESI+[M+H]$^+$ m/z=412.9).

This set of examples illustrates the easiness of amine or alcohol loading on activated pipecolic linker, and the flexibility of this new linker for solid phase synthesis.

III.6 Cleavage Kinetics Studies

The cleavage procedure used in previous assays was 100% TFA treatment for 90 minutes, based on the Inventors' observations during synthesis of libraries in side arylpiperazine series (Zajdel et al., 2004). However, further investigations were performed to investigate the acid sensitivity of the pipecolic linker. Experiments were set up for the cleavage of resin 2 for amide, 14 and 18 for ester bonds.

100 mg of resins 2, 14 or 18 were poured into vials containing 5 mL of one of the following cleavage solutions: 100% TFA, 10% TFA in DCM, 1% TFA in DCM, 95% AcOH, and 10% AcOH in DCM. Aliquots of solution (100 µl) were collected at different times for 24 hours and analyzed by HPLC. Areas of the peak at 301 nm, corresponding to released Fmoc-1-amino-3-aminopropane from resin 2, Fmoc-Ser-OMe (15) released from resin 14, and Fmoc-Tyr-OMe (19) from resin 18 were measured and data was collected. Curves are reported in FIGS. 1 to 3.

An ester and an amide linkage showed nearly the same behavior upon acidic conditions. Generally, the pipecolic linker is not stable in acidic conditions; i.e. after 1 h treatment with TFA of the amide and ester linkage almost 80% of the product was released from the resin, while the product was liberated from the support after 12 h treatment with neat TFA.

The linkage was also not totally stable in 1% TFA, since after one hour treatment an amount of 10% of the product was released from the support. It is also worth noting that one hour treatment of the resin with the mixture of 10% AcOH in DMF resulted in the cleavage of 70% N-Fmoc amino acid methyl ester attached to the support. Surprisingly, one hour treatment of the amide linkage with 95% AcOH released only 22% of N-Fmoc amino acid methyl ester. Further treatment for 12 and 24 hours resulted in cleavage of 65% and 80% of the compound, respectively. This was probably due to the fact that neat acetic acid did not swell sufficiently PS resin.

IV: Conclusion

This piece of work presents the design of a new linker based on pipecolic acid. Upon acid treatment, a mechanism involving a oxazolinium-5-one (munchnone) intermediate cleaving an amide bond or an ester is releasing a primary amine or an alcohol in solution. The Inventors demonstrated the effectiveness of the pipecolic linker to anchor amines and alcohol thought activation of supported the carboxylic acid function. Kinetic cleavage studies clearly showed the acid-lability of this linker, which could be used as an alternative to the trityl linker in Fmoc based protecting strategies. Examples of reverse SPPS, pseudopeptide synthesis and amino acid side chain anchoring illustrated the versatility of this new linker. Regarding the very straightforward anchoring strategy, attachment of other nucleophiles to solid support via pipecolic handle is currently under investigations in the laboratory.

BIBLIOGRAPHIC REFERENCES

Boschi, D.; Tron, G. C.; Lazzarato, L.; Chegaev, K.; Cena, C.; Di Stilo, A.; Giorgis, M.; Bertinaria, M.; Fruttero, R.; Gasco, A. *Journal of Medicinal Chemistry* 2006, 49, 2886-2897.

Nam, N.-H.; Sardari, S.; Parang, K. *Journal of Combinatorial Chemistry* 2003, 5, 479-546.

Stromgaard, K.; Andersen, K.; Ruhland, T.; Krogsgaard-Larsen, P.; Jaroszewski, J. W. *Synthesis* 2001, 877-884.

Albericio, F.; Frieden, A.; Del Fresno, M.; Royo, M.; Alsina, J.; Jensen, K. J.; Kates, S. A.; Barany, G. *Innovation and Perspectives in Solid Phase Synthesis & Combinatorial Libraries Peptides, Proteins and Nucleic Acids—Small Molecule Organic Chemical Diversity, Collected Papers, International Symposium,* 5th, London, Sep. 2-6, 1997 1999a, 7-10.

Alsina, J.; Yokum, T. S.; Albericio, F.; Barany, G. *Journal of Organic Chemistry* 1999, 64, 8761-8769.

Jensen, K. J.; Alsina, J.; Songster, M. F.; Vagner, J.; Albericio, F.; Barany, G. *Journal of the American Chemical Society* 1998, 120, 5441-5452.

Albericio, F.; Del Fresno, M.; Frieden, A.; Royo, M.; Alsina, J.; Jensen, K. J.; Kates, S. A.; Barany, G. *Peptides: Frontiers of Peptide Science, Proceedings of the American Peptide Symposium,* 15th, Nashville, Jun. 14-19, 1997 1999b, 37-39.

Hamze, A.; Martinez, J.; Hernandez, J.-F. *Journal of Organic Chemistry* 2004, 69, 8394-8402.

Subra, G.; Amblard, M.; Martinez, J. *Tetrahedron Letters* 2002, 43, 9221-9223.

Cantel, S.; Heitz, A.; Martinez, J.; Fehrentz, J.-A. *Journal of Peptide Science* 2004, 10, 531-534.

Cantel, S.; Boeglin, D.; Rolland, M.; Martinez, J.; Fehrentz, J.-A. *Tetrahedron Letters* 2003, 44, 4797-4799.

Zajdel, P.; Subra, G.; Bojarski Andrzej, J.; Duszynska, B.; Pawlowski, M.; Martinez, J. *Journal of Combinatorial Chemistry* 2004, 6, 761-767.

Wei, L.; Wu, Y.-Q.; Wilkinson, D. E.; Chen, Y.; Soni, R.; Scott, C.; Ross, D. T.; Guo, H.; Howorth, P.; Valentine, H.; Liang, S.; Spicer, D.; Fuller, M.; Steiner, J.; Hamilton, G. S. *Bioorganic & Medicinal Chemistry Letters* 2002, 12, 1429-1433.

Maison, W.; Lutzen, A.; Kosten, M.; Schlemminger, I.; Westerhoff, O.; Martens, J. *Journal of the Chemical Society, Perkin Transactions* 1: *Organic and Bio-Organic Chemistry* 1999, 3515-3525.

Attardi, M. E.; Porcu, G.; Taddei, M. *Tetrahedron Letters* 2000, 41, 7391-7394.

Barlos, K.; Gatos, D.; Kallitsis, I.; Papaioannou, D.; Sotiriou, P. *Liebigs Annalen der Chemie* 1988, 1079-81.

Bernhardt, A.; Drewello, M.; Schutkowski, M. *The Journal of Peptide Research* 1997, 50, 143-152.

Gutheil, W. G.; Xu, Q. In *PCT Int. Appl.*; (The Curators of the University of Missouri, USA). Wo, 2002, p 30 pp.

Gutheil, W. G.; Xu, Q. *Chemical & Pharmaceutical Bulletin* 2002, 50, 688-691.

Johansson, A.; Akerblom, E.; Ersmark, K.; Lindeberg, G.; Hallberg, A. *Journal of Combinatorial Chemistry* 2000, 2, 496-507.

The invention claimed is:

1. A solid phase-linker combination having the following formula:

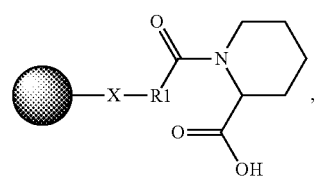

(I)

wherein

represents a solid support used in organic synthesis,

X is absent or represents —NR$_2$—, —NR$_2$—CO—, —S—CO—, —O—, —CO—NR$_2$—, —S—, —CO—S—, —CO—O—, —O—CO—, —SO$_2$—NR$_2$— or —NR$_2$SO$_2$— wherein R$_2$ represents H or a (C$_1$-C$_6$) alkyl, advantageously H, it being understood that X can be separated from the solid support by means of a spacer, and R$_1$ represents a branched (C$_3$-C$_{30}$) alkyl group, a branched (C$_3$-C$_{30}$) alkenyl group, a branched (C$_3$-C$_{30}$) alkynyl group, a (C$_4$-C$_{12}$) monocyclic or polycyclic cycloalkyl group, a (C$_1$-C$_6$) alkyl-(C$_4$-C$_{12}$) monocyclic or polycyclic cycloalkyl group, a (C$_2$-C$_6$) alkenyl-(C$_4$-C$_{12}$) monocyclic or polycyclic cycloalkyl group, or a (C$_2$-C$_6$) alkynyl-(C$_4$-C$_{12}$) monocyclic or polycyclic cycloalkyl group.

2. The solid phase-linker combination of formula (I) according to claim 1, wherein X represents —NH—CO— or —CO—NH—.

3. The solid phase-linker combination of formula (I) according to claim 1, which is represented by the formula selected from the following formulae:

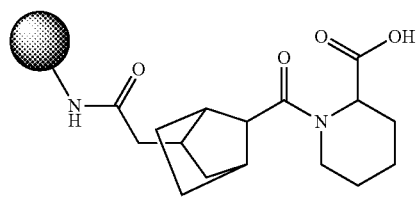

(Ia)

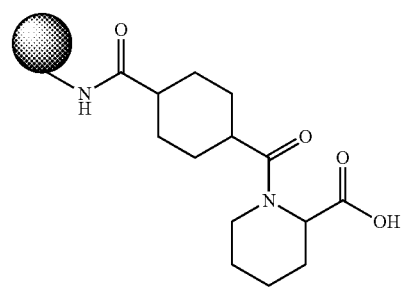

(Ib)

(Ic)

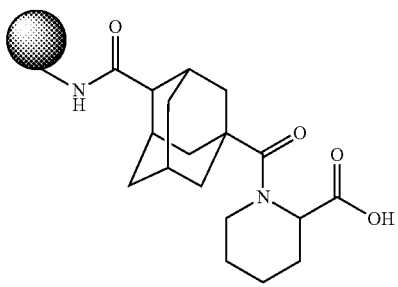

wherein

is as defined in claim 1.

4. A method for chemical synthesis which comprises forming a solid phase-linker combination by attaching a solid phase linker having the following formula:

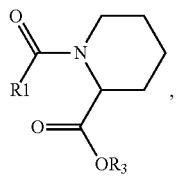
(XI)

wherein $R_1$ is as defined in claim 1 and $R_1$ is advantageously functionalized with a functional group Y, which is selected from the group consisting of —OH, COOH, —$NHR_2$, —$SO_2$, —$SO_3H$, and —SH, wherein $R_2$ is a $C_1$-$C_6$ alkyl, and $R_3$ represents an O-protecting group to a solid phase through $R_1$; deprotecting the O group containing $R_3$; and reacting the deprotected O group with another compound.

5. The method according to claim 4, which comprises coupling to the deprotected O group to functional groups on another compound, wherein the functional groups are selected from the group consisting of primary amines, secondary amines, aromatic amines, alcohols, phenols, and thiols.

6. The method according to claim 4, which comprises reverse synthesizing an N to C peptide, synthesizing a C to N peptide, synthesizing a pseudopeptide or synthesizing a retro-inverso peptide.

7. The method according to claim 4 which comprises synthesizing small organic molecules.

8. A method of reverse N to C peptide synthesis comprising the following successive steps:
(a2) coupling the solid phase linker combination of formula (I) according to claim 1 with a COO-protected amino acid in which the reactive functions of the amino acid lateral chains are protected in order to obtain a COO-protected amino acids coupled with the solid phase linker combination,
(b2) COO-deprotecting the amino acid coupled with the solid phase linker combination,
(c2) coupling the COO-deprotected amino acid coupled with the solid phase linker combination obtained in step (b2) with an additional COO-protected amino acid, which may be the same or different from the COO-protected amino acid of step (a2) and in which the reactive functions of the amino acid lateral chains are protected in order to obtain COO-protected peptides coupled with the solid phase linker combination,
(d2) optionally repeating steps (b2) and (c2) as many times as necessary in order to obtain a solid phase linker combination loaded with peptidic chains,
(e2) cleaving the bond between the solid phase linker combination and the peptidic chains in order to recover the solid phase linker combination of formula (I) and peptidic chains.

9. The method according to claim 8, wherein it comprises, before or after step (e2), a further step (f2) of deprotecting the amino acid lateral chains of the peptidic chains and/or COO-deprotecting the peptidic chains.

10. The method according to claim 8, wherein the coupling step (a2) and/or (c2) is carried out under N-[(dimethylamino)-1H-1,2,3-triazolo-[4,5-b]pyridine-1-yl-methylene]-N-methylmethanaminium hexafluorophosphate N-oxide activation in the presence of 2,4,6 trimethylpyridine in a solvent such as dimethylformamide, in order to avoid amino acid epimerization.

11. The method according to claim 10, wherein the solvent is dimethylformamide.

12. A method of C to N peptide synthesis comprising the following successive steps:
(a3) coupling the solid phase-linker combination of formula (I) according to claim 1 with N-protected and a COO-protected amino acid whose lateral chains carry an unprotected group selected among an hydroxyl group, an amine group and a thiol group, in order to obtain N-protected and a COO-protected amino acid coupled with the solid phase linker combination,
(b3) N-deprotecting the COO-protected amino acid coupled to the solid phase linker combination in order to obtain an N-deprotected COO-protected amino acid coupled to the solid phase linker combination,
(c3) coupling the coupled N-deprotected COO-protected amino acids with an additional N-protected amino acid which may be the same or different from the COO-protected amino acid of step (a3) and in which the reactive functions of the amino acid lateral chains are protected in order to obtain N-protected COO-protected peptides coupled with the solid phase linker combination,
(d3) N-deprotecting the coupled COO-protected peptides obtained in step (c3),
(e3) optionally repeating steps (c3) and (d3) as many times as necessary in order to obtain a solid phase linker combination of formula (I) loaded with peptidic chains,
(f3) cleaving the bond between the solid phase linker combination and the peptidic chains in order to recover the solid phase linker combination of formula (I) and peptidic chains.

13. The method according to claim 12, wherein it comprises before or after step (f3), a further step (g3) of deprotecting the amino acid lateral chains of the peptidic chains and/or COO-deprotecting the peptidic chains.

14. The method according to claim 12, wherein the N— and COO-protected amino acids whose lateral chains carry an unprotected group of step (a3) are selected from:
the N-protected and COO-protected amino acids which carry an hydroxyl group,
the N-protected and COO-protected amino acids which carry an amine group, and the N-protected and COO-protected amino acids which carry a thiol group.

15. The method according to claim 14, wherein the N-protected and COO-protected amino acids which carry an hydroxyl group are threonine, serine or tyrosine.

16. The method according to claim 14, wherein the N-protected and COO-protected amino acids which carry an amine group are lysine, ornithine, diaminobutyric acid or diaminopropionic acid.

17. The method according to claim 14, wherein the N-protected and COO-protected amino acids which carry a thiol group is cysteine.

18. A method of retro-inverso peptide synthesis comprising the following successive steps:
(a4) coupling a compound of formula

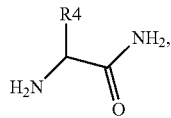
(VII)

wherein $R_4$ represents the lateral chain of an amino acid in which the reactive functions are protected,
with the solid phase linker combination of formula (I) according to claim 1 in order to obtain a solid phase linker combination of formula

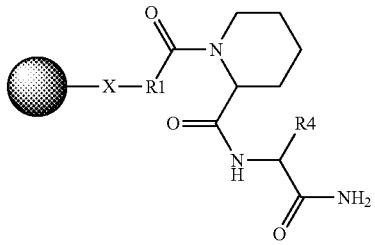
(VIII)

wherein

,

X and $R_1$ are as defined in claim 1 and $R_4$ is as defined above, (b4) treating the solid phase linker combination of formula (VIII) obtained in step (a4) in order to obtain a solid phase linker combination of formula

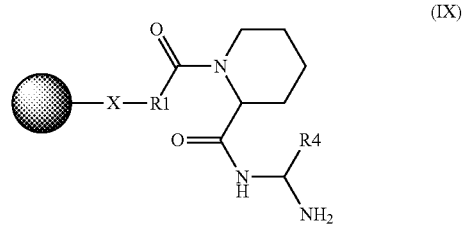
(IX)

wherein

,

X, $R_1$ and $R_4$ are as defined above,
(c4) coupling the solid phase linker combination of formula (IX) obtained in step (b4) with an N-protected amino-acid in which the reactive functions of the amino acid lateral chains are protected in order to obtain an N-protected amino acid acids coupled to the solid phase linker combination of formula (IX),
(d4) N-deprotecting the coupled amino acid,
(e4) coupling the N-deprotected coupled amino acid of step (d4) with an additional N-protected amino acid, which may be the same or different from the N-protected amino acid of step (c4) and in which the reactive functions of the amino acid lateral chains are protected in order to obtain an N-protected peptide coupled with the solid phase linker combination of formula (IX),
(f4) optionally repeating steps (d4) and (e4) as many times as necessary in order to obtain a solid phase linker combination of formula (I) loaded with retro-inverso peptidic chains,
(g4) cleaving the bond between the solid phase linker combination and the peptidic chains in order to recover the solid phase linker combination of formula (I) and peptidic chains.

19. The method according to claim 18, wherein it comprises, before or after step (g4), a further step (h4) of deprotecting the amino acid lateral chains of the peptidic chains and/or N-deprotecting the peptidic chains.

* * * * *